(12) United States Patent
Robl

(10) Patent No.: US 6,777,550 B1
(45) Date of Patent: Aug. 17, 2004

(54) N-FORMYL HYDROXYLAMINE CONTAINING COMPOUNDS USEFUL AS ACE INHIBITORS AND/OR NEP INHIBITORS

(75) Inventor: Jeffrey A. Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 08/833,172

(22) Filed: Apr. 4, 1997

Related U.S. Application Data

(60) Provisional application No. 60/016,295, filed on Apr. 12, 1996.

(51) Int. Cl.[7] .................... C07D 223/12; C07D 223/16; C07D 267/02; A61K 31/553; A61K 31/55
(52) U.S. Cl. .................. 540/527; 540/491; 540/522
(58) Field of Search .................... 540/527; 514/212

(56) References Cited

U.S. PATENT DOCUMENTS

| | | | |
|---|---|---|---|
| 4,996,358 A | 2/1991 | Handa et al. | 562/621 |
| 5,484,917 A | * 1/1996 | Lowe, III | 540/527 |

FOREIGN PATENT DOCUMENTS

| | | |
|---|---|---|
| EP | 0 236 872 A2 | 9/1987 |
| EP | 0534363 A2 | 9/1992 |
| EP | 0 524 553 A1 | 1/1993 |
| EP | 0599444 A1 | 5/1993 |
| EP | 0 599 444 A1 | 6/1994 |
| EP | 0629627 A2 | 6/1994 |
| EP | 0 655 461 A1 | 5/1995 |

OTHER PUBLICATIONS

Nishino et al, "*Pseudomonas aeruginosa* Elastase Development of a new substrate, Inhibitors, and an Affinity Ligand", The Journal of Biological Chemistry, vol. 255, No. 8, Apr. 25, pp. 3482–3486, 1980.

Nishino et al, "Design of Potent Reversible Inhibitors for Thermolysin. Peptides Containing Zinc Coordinating Ligands and Their Use in Affinity Chromatography" American Chemical Society, vol. 18, No. 20, pp. 4340–4347, 1979.

Weller et al, "Design of Conformationally Constrained Angiotensin–Converting Enzyme Inhibitors" Biochemical and Biophysical Research Communications, vol. 125, No. 1, pp. 82–89, Nov. 30, 1984.

Weller et. al. Biochemical & Biophysical Research Communication. vol. 125. No. 1, (1984) pgs. 82–89.

Fournie–Zaluski, et al. Journal of Medicianl Chemistry, vol. 28, No. 9, (1985) Pps. 1158–1169.

Nishino et al. Biochemistry, vol. 18, No. 20, (1979), pp. 4340–4347.

* cited by examiner

*Primary Examiner*—Mark L. Berch
(74) *Attorney, Agent, or Firm*—Burton Rodney

(57) ABSTRACT

N-formyl hydroxylamines are provided which have the structure

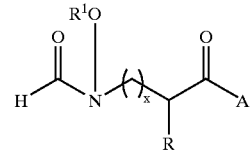

wherein R is H, alkyl, alkenyl, aryl-$(CH_2)_p$—, heteroaryl-$(CH_2)_p$— or cycloheteroalkyl-$(CH_2)_p$—

$R^1$ is H or $COR^2$ where $R^2$ is alkyl, aryl-$(CH_2)_p$—, cycloheteroalkyl-$(CH_2)_p$—, heteroaryl-$(CH_2)_p$—, alkoxy or cycloalkyl-$(CH_2)_p$—, p is 0 to 8, and A is a dipeptide derived from an amino acid or is a conformationally restricted dipeptide mimic.

The above compounds are useful in treating hypertension congestive heart failure, renal failure, and hepatic cirrhosis.

2 Claims, No Drawings

N-FORMYL HYDROXYLAMINE CONTAINING COMPOUNDS USEFUL AS ACE INHIBITORS AND/OR NEP INHIBITORS

This application claims benefit of Provisional Application No. 60/016,295 filed Apr. 12, 1996.

SUMMARY OF THE INVENTION

This invention is directed to novel compounds possessing angiotensin converting enzyme (ACE) inhibitory activity and/or neutral endopeptidase (NEP) inhibitory activity and methods of preparing such compounds. This invention is also directed to pharmaceutical compositions containing such ACE and/or NEP inhibiting compounds or pharmaceutically acceptable salts thereof and the method of using such compositions.

The compounds of this invention are those of the formula (I)

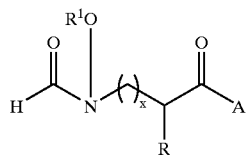

I including a pharmaceutically acceptable salt thereof where:

x is 0 or 1;

R is H, alkyl, alkenyl, aryl-$(CH_2)_p$—, heteroaryl-$(CH_2)_p$—, cycloheteroalkyl-$(CH_2)_p$—, or R can be joined together with the carbon to which it is attached to form a 3 to 7 membered ring which may optionally be fused to a benzene ring;

$R^1$ is H or —$COR^2$ where $R^2$ is alkyl, aryl-$(CH_2)_p$—, cycloheteroalkyl-$(CH_2)_p$—, heteroaryl-$(CH_2)_p$—, alkoxy, or cycloalkyl-$(CH_2)_p$—;

p is 0 or an integer from 1 to 8; and

A is a dipeptide derived from one or two non-proteinogenic amino acid or is a conformationally restricted dipeptide mimic as described below.

A is a dipeptide derivative of the structure

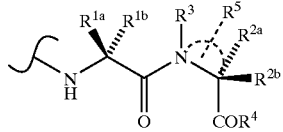

A(1)

where $R^{1a}$, $R^{1b}$, $R^{2a}$ and $R^{2b}$ are independently selected from H, alkyl, aryl-$(CH_2)_p$—, cycloalkyl, cycloheteroalkyl-$(CH_2)_p$—, heteroaryl-$(CH_2)_p$—, biphenylmethyl, or $R^{1a}$ and $R^{1b}$ or $R^{2a}$ and $R^{2b}$ may be joined together to the carbon to which they are attached to form a 3 to 7 membered ring, optionally fused to a benzene ring; and

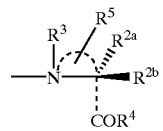

refers to an optional 5 or 6 membered ring containing a single hetero atom and which may optionally include an $R^5$ substituent (as shown) which is H, alkyl, aryl-$(CH_2)_p$ or cycloalkyl-$(CH_2)_p$, cycloheteroalkyl-$(CH_2)_p$, or cycloheteroaryl-$(CH_2)_p$—;

$R^3$ is H, alkyl or aryl-$(CH_2)_p$—;

$R^4$ is OH, Oalkyl, O—$(CH_2)_p$aryl- or $NR_1(R_2)$ where $R_1$ and $R_2$ are independently H, alkyl, or aryl$(CH_2)_p$ or heteroaryl-$(CH_2)_p$—;

with the proviso that in A(1) at least one of

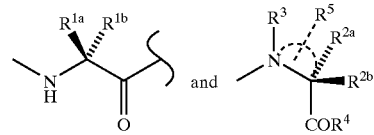

is other than a natural α-amino acid, and thus must be other than valine, leucine, phenylalanine, tyrosine, serine, cysteine, threonine, methionine, aspartic acid, glutamic acid, arginine, lysine or proline.

In addition, A can be a conformationally restricted dipeptide mimic which has the structure

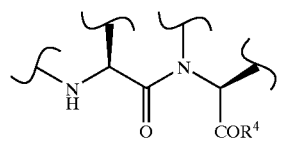

A(2)

and is a non-proteinogenic dipeptide.

Thus, the compound of formula I include

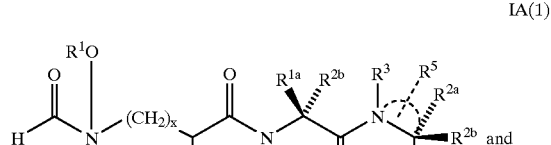

IA(1)

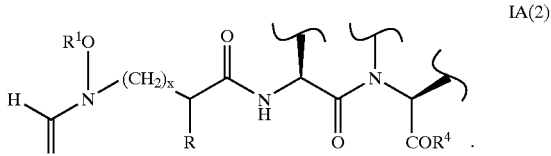

IA(2)

The term "conformationally restricted dipeptide mimic" refers to a structural skeleton which has the attributes of a conventional dipeptide

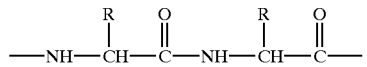

but having enhanced biological properties due to additional bonds which limit the rotational freedom.

Examples of the A(2) dipeptide mimics include any of the conformationally restricted dipeptide mimics set out below.

A(3)
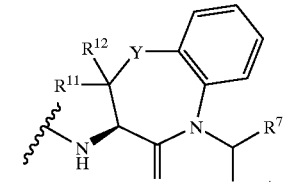
where Y = O, S, $CH_2$
or $S(O)_{0,1,2}$

A(4)
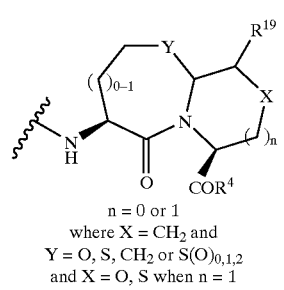
n = 0 or 1
where X = $CH_2$ and
Y = O, S, $CH_2$ or $S(O)_{0,1,2}$
and X = O, S when n = 1

A(5)
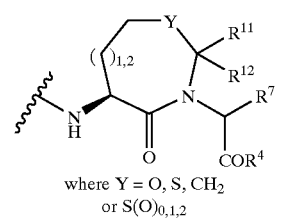
where Y = O, S, $CH_2$
or $S(O)_{0,1,2}$

A(6)
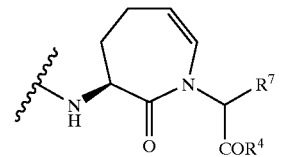

A(7)
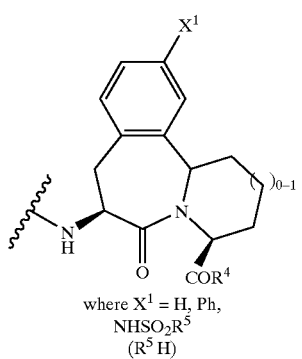
where $X^1$ = H, Ph,
$NHSO_2R^5$
($R^5$ H)

A(8)
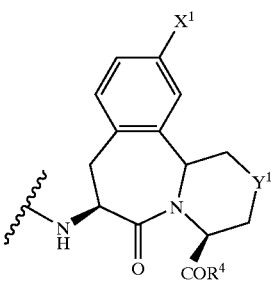
where $Y^1$ = O, S, NH
or $S(O)_n$,
where $X^1$ = H, Ph,
$NHSO_2R^5$
($R^5$ H)

A(9)
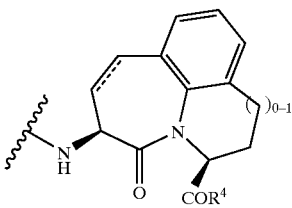

A(10)
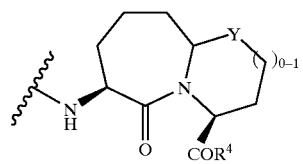
where Y = O, S, $CH_2$
or $S(O)_{0,1,2}$

A(11)
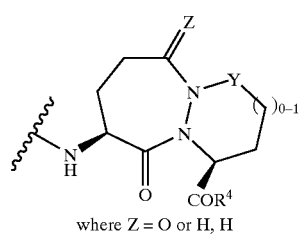
where Z = O or H, H

A(12)
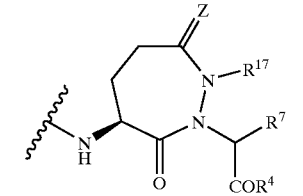
where Z = O or H, H

A(13)
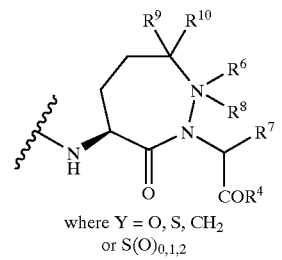
where Y = O, S, $CH_2$
or $S(O)_{0,1,2}$

A(14)

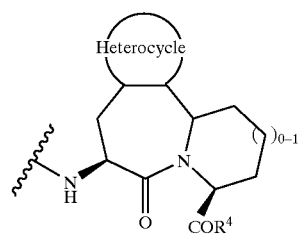

A(15)

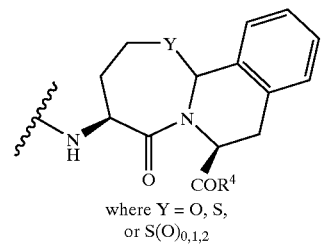
where Y = O, S, or S(O)$_{0,1,2}$

A(16)

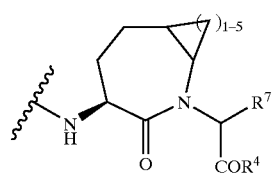

A(17)

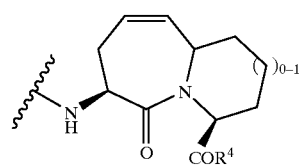

A(18)

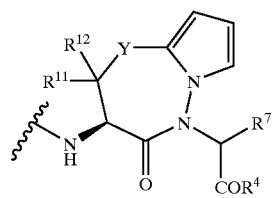
where Y = O, S, CH$_2$

A(19)

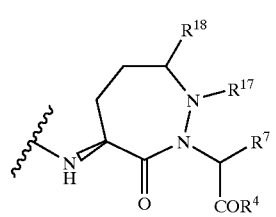

A(20)

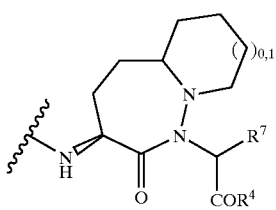

A(21)

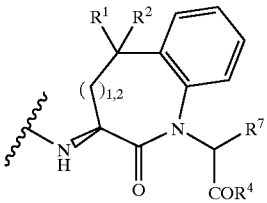

A(22)

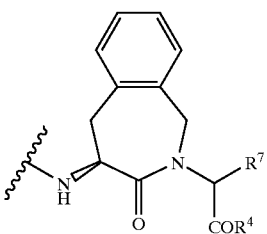

A(23)

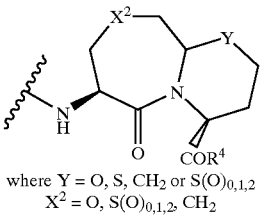
where Y = O, S, CH$_2$ or S(O)$_{0,1,2}$
X$^2$ = O, S(O)$_{0,1,2}$, CH$_2$ With respect to A(5), $R^{11}$ and $R^{12}$ are independently selected from hydrogen, alkyl, substituted alkyl, alkenyl, substituted alkenyl, cycloalkyl-(CH$_2$)$_m$—, aryl-(CH$_2$)$_m$—, substituted aryl-(CH$_2$)$_m$—, and heteroaryl-(CH$_2$)$_m$—, or $R^{11}$ and $R^{12}$ taken together with the carbon to which they are attached complete a saturated cycloalkyl ring of 3 to 7 carbons, or $R^{11}$ and $R^{12}$ taken together with the carbon to which they are attached complete a keto substituent, i.e.,

with respect to A(13) $R^8$, $R^9$ and $R^7$ are independently selected from hydrogen, alkyl, substituted alkyl, alkenyl, substituted alkenyl, cycloalkyl-(CH$_2$)$_m$—, aryl-(CH$_2$)$_m$—, substituted aryl-(CH$_2$)$_m$—, and heteroaryl-(CH$_2$)$_m$—;

$R^{10}$ and $R^6$ are independently selected from hydrogen, alkyl, substituted alkyl, alkenyl, substituted alkenyl, cycloalkyl-(CH$_2$)$_m$—, aryl-(CH$_2$)$_m$, substituted aryl-(CH$_2$)$_m$—, and heteroaryl-(CH$_2$)$_m$—, or $R^6$ and $R^{10}$ taken together with the carbon to which they are attached complete a saturated cycloalkyl ring of 3 to 7 carbons, $R^6$ and $R^8$ taken together with the carbon to which they are attached complete a saturated cycloalkyl ring of 3 to 7 carbons, or $R^9$ and $R^{10}$ taken together with the carbon to which they are attached complete a saturated cycloalkyl ring of 3 to 7 carbons;

m is zero or an integer from 1 to 6;

$R^4$ is OH, Oalkyl, O—$(CH_2)_m$-heteroaryl,

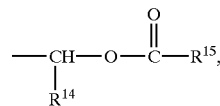

O—$(CH_2)_m$-aryl, or

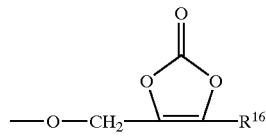

or $NR_1(R_2)$;

where $R_1$ and $R_2$ are independently H, alkyl, aryl$(CH_2)_p$, aryl or heteroaryl;

$R^{14}$ is hydrogen, lower alkyl, cycloalkyl, or phenyl;

$R^{15}$ is hydrogen, lower alkyl, lower alkoxy or phenyl;

$R^{16}$ is alkyl or aryl-$(CH_2)_m$—; and $R^{17}$ is hydrogen, alkyl, substituted alkyl, alkenyl, substituted alkenyl, cycloalkyl-$(CH_2)_m$—, aryl-$(CH_2)_m$—, substituted aryl-$(CH_2)_m$—, or heteroaryl-$(CH_2)_m$—.

$R^{18}$ is H, alkyl or alkenyl, and $R^{18}$ and $R^{17}$ may be taken together with the carbon and nitrogen to which they are attached to complete a saturated N-containing ring of 5 or 6 ring members.

$R^{19}$ is H or an alkyl, and in A(4), $R^{19}$ and x (which is $CH_2$) together with the carbons to which they are attached may form an aromatic ring of carbons (as in A(15)).

The starting compounds H-A(1) and H-A(2) are described in the literature or are obtained by modifications of known procedures. For example, the starting compounds of formula H-A(1) or H-A(2) wherein A(1) or A(2) is as defined in formulas A(5), A(13), A(16), A(21), where Y (where present) is $CH_2$ are disclosed by Thorsett et al., J. Med. Chem., 29, p. 251–260 (1988), Harris et al. in U.S. Pat. Nos. 4,587,050, 4,587,238, 4,629,787 and Yanagisawa et al. in U.S. Pat. No. 4,734,410.

The starting compounds of formula H-A(1) or H-A(2) wherein A(1) or A(2) is as defined in formulas A(3) and A(13) where Y is S(O)n are disclosed by Yanagisawa et al., J., Med. Chem., 30, p. 1984–1991 (1987) and 31, p. 422–428 (1988), Karanewsky in U.S. Pat. No. 4,460,579, Cheung et al. in U.S. Pat. No. 4,594,341, and Yanagisawa et al. in U.S. Pat. No. 4,699,905.

The starting compounds of formula H-A(1) or H-A(2) wherein A(1) or A(2) is as defined in formula A(5) are disclosed by Karanewsky in U.S. Pat. Nos. 4,460,579 and 4,711,884.

The starting compounds of formula H-A(1) or H-A(2) wherein A(1) or A(2) is as defined in formulas A(3) (Y is —$CH_2$—, and A(21) are disclosed by Watthey et al., J. Med. Chem., 28, p. 1511–1516 (1985) and Watthey in U.S. Pat. Nos. 4,410,520, 4,470,988, 4,473,575, 4,537,885 and 4,575,503 and also by Parsons et al., Biochemical & Biophysical Research Comm., 117, p. 108–113 (1983) and in U.S. Pat. No. 4,873,235.

The starting compounds of formula H-A(1) or H-A(2) wherein A(1) or A(2) is as defined in formula A(3) and Y is S or O are disclosed by Slade et al., J. Med. Chem., 28, p. 1517–1521 (1985) and in U.S. Pat. No. 4,477,464 and Itoh et al., Chem. Pharm. Bull., 34, p. 1128–1147 (1986) and 34, p. 2078–2089 (1986) as well as Sugihara et al. in U.S. Pat. No. 4,548,932 (Y is O) and Katakami et al. in U.S. Pat. No. 4,539,150 (Y is S).

The starting compounds of formula H-A(1) or H-A(2) wherein A(1) or A(2) is as defined in formula A(16) can be prepared by reduction of the corresponding starting compounds wherein A(1) or A(2) is as defined in formula A(3).

The starting compounds of formula H-A(1) or H-A(2) wherein A(1) or A(2) is as defined in formula A(22) are disclosed by Flynn et al in U.S. Pat. No. 4,973,585.

The starting compounds of formula H-A(1) or H-A(2) wherein A(1) or A(2) is as defined in formula A(10) and Y is S, —SO, or —$SO_2$ are disclosed by Harris et al. and Patchett et al. in U.S. Pat. Nos. 4,415,496 and 4,617,301.

The starting compounds of formula H-A(1) or H-A(2) wherein A(1) or A(2) is as defined in formula A(10) and Y is $CH_2$, and is as defined in formula A(23) where $X^2$ is $CH_2$ is disclosed by Thorsett, Actual. Chim. Ther., 13, p. 257–268 (1986).

The starting compounds of formula H-A(1) or H-A(2) wherein A(1) or A(2) is as defined in formulas A(11) and A(19) and A(20) are disclosed by Attwood et al., Federation of European Biochemical Studies, 165, p. 201–206 (1984) and in U.S. Pat. No. 4,512,994 and Natoff et al., Drugs Of The Future, 12, p. 475–483 (1987).

The starting compounds of formula H-A(1) or H-A(2) wherein A(1) or A(2) is as defined in formula A(12) are disclosed by Huang et al. in U.S. Pat. No. 4,465,679.

The starting compounds of formula H-A(1) or H-A(2) wherein A(1) or A(2) is as defined in formula A(18) are disclosed by Bolos et al. in Tetrahedron, 48, p. 9567–9576 (1992).

The starting compounds of formula H-A(1) or H-A(2) wherein A(1) or A(2) is as defined in formulas A(4) and A(15) are disclosed in European Patent Application 0629627A2.

The starting compounds of formula H-A(1) or H-A(2) wherein A(1) or A(2) is as defined in formula A(9) are disclosed in U.S. application Ser. No. 100,408 (file HA611).

The starting compounds of formula H-A(1) or H-A(2) wherein A(1) or A(2) is as defined in formulas A(7) and A(8) are disclosed in European Patent Application 481,522 (Flynn et al) and European Patent Application 0534363A2 (Warshawsky et al).

The starting compounds of formula H-A(1) or H-A(2) wherein A(1) or A(2) is as defined in formula A(14) are disclosed in U.S. application Ser. No. 153,854 (file HA615).

The starting compounds of formula H-A(1) or H-A(2) wherein A(1) or A(2) is as defined in formula A(17) are disclosed in European Patent Application 0599444A1 (Barrish et al).

In addition, in accordance with the present invention, a pharmaceutical composition is provided which includes a therapeutically effective amount of compound I and a pharmaceutically acceptable carrier therefor.

The pharmaceutical composition as defined above will be useful in the treatment of cardiovascular diseases such as hypertension and/or congestive heart failure.

Furthermore, in accordance with the present invention, a method is provided for treating a cardiovascular disease such as hypertension and/or congestive heart failure, as well as other diseases as set out hereinafter, which includes the step of administering to a mammalian species, including humans, dogs and cats, a therapeutically effective amount of a composition as defined above.

DETAILED DESCRIPTION OF THE INVENTION

The term "alkyl" or "lower alkyl" refers to straight or branched chain radicals having up to and including ten carbon atoms, preferably up to and including six carbon atoms, which may optionally include one, two, or three substituents including a hydroxy, amino, alkyl, cycloalkyl, aryl, halo, trifluoromethyl, cyano, —NH(lower alkyl), —N(lower alkyl)$_2$, lower alkoxy, lower alkylthio, carboxy or heteroaryl.

The term "alkenyl" refers to straight or branched chain radicals of 3 to 10 carbon atoms having one or two double bonds, preferably straight chain radicals of 3 to 5 carbons having one double bond, which may optionally be substituted with one, two or three substituents including alkyl, aryl, cycloalkyl, hydroxy, amino, halo, trifluoromethyl, cyano, —NH(lower alkyl), —N(lower alkyl)$_2$, lower alkoxy, lower alkylthio, carboxy or heteroaryl.

The terms "alkoxy" or "lower alkoxy" and "alkylthio" or "lower alkylthio" refer to such alkyl groups as defined above attached to an oxygen or sulfur.

The term "cycloalkyl" refers to saturated rings of 3 to 7 carbon atoms.

The term "halo" refers to chloro, bromo, fluoro, and iodo.

The term "aryl" refers to aromatic groups containing 6 to 10 carbons, preferably phenyl, 1-naphthyl, and 2-naphthyl, which may optionally contain one, two or three substituents selected from alkyl, alkoxy, alkylthio, halo, hydroxy, trifluoromethyl, —SO$_2$NH$_2$, amino, —NH(lower alkyl), or —N(lower alkyl)2, di- and tri-substituted phenyl, 1-naphthyl, or 2-naphthyl, wherein said substituents are preferably selected from methyl, methoxy, methylthio, halo, hydroxy, and amino.

The term "heteroaryl" refers to unsaturated rings of 5 or 6 atoms containing one or two O and S atoms and/or one to four N atoms provided that the total number of hetero atoms in the ring is 4 or less, which may optionally be substituted with one, two or three substituents which include alkyl, aryl, cycloalkyl, alkoxy or halo. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term heteroaryl also includes bicyclic rings wherein the five or six membered ring containing O, S, and N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl, or cyclohexylmethyl. Also, if the mono or bicyclic ring has an available N-atom such N atom can also be substituted by an N-protecting group such as

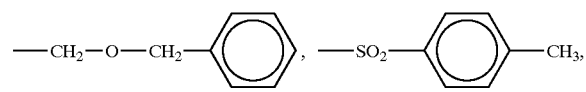

2,4-dinitrophenyl, lower alkyl, benzyl, or benzhydryl.

The compounds of formula I of the invention may be prepared as outlined in Reaction Scheme I set out below (where x is 0 or 1).

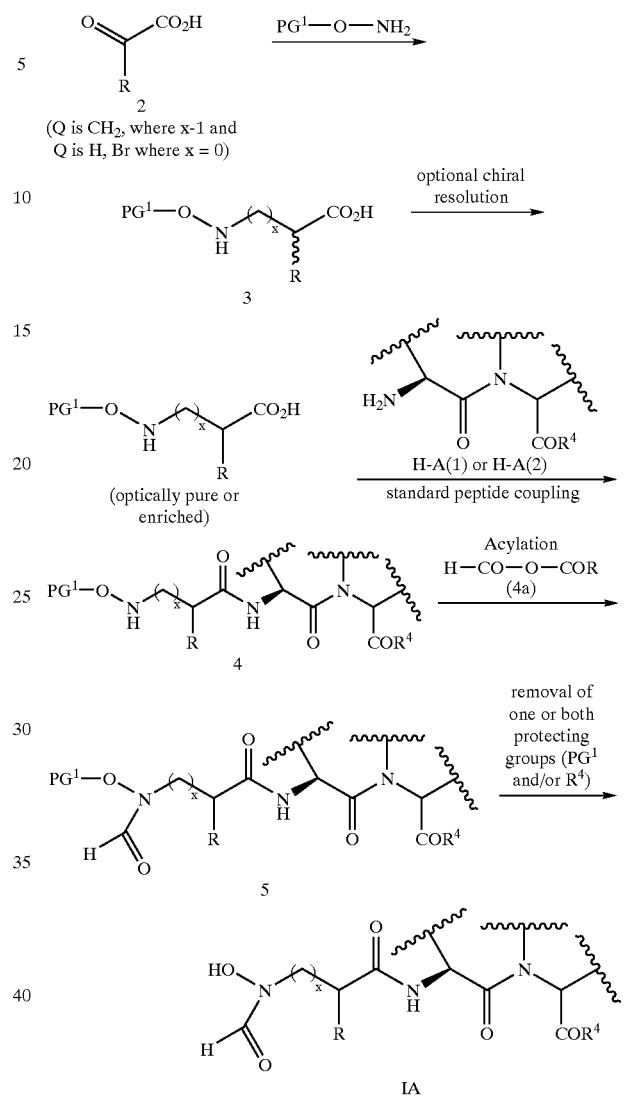

As shown in Scheme I, acid 2 may be reacted with a suitably O-protected (e.g. PG$^1$ is benzyl, p-methoxybenzyl, tetrahydropyranyl, trityl, benzhydryl, etc.) hydroxylamine to give the adduct 3. Compound 3 may be coupled directly with amine H-A(1) or H-A(2) to give a mixture of diastereomers which may be separated or preferably compound 3 may be optically enriched or purified, employing conventional techniques, to give 3*. Subsequent coupling with H-A(1) or H-A(2) gives 4 in diastereomerically enriched or pure form. Reaction of the hydroxylamine nitrogen of 4 with a formylating agent affords 5. At this point one or both protecting groups may be removed, either sequentially or simultaneously, to produce compound of the invention IA. For example, when PG$^1$ is benzyl and R$^4$ is Obenzyl, both may be removed by hydrogenolysis. When PG$^1$ is benzyl and R$^4$ is $^-$Omethyl or $^-$Oethyl, the PG$^1$ group may be removed by hydrogenolysis and the ester group may be converted to the acid by base hydrolysis. PG$^1$ groups such as THP or trityl may be removed by treatment with strong acid such as hydrogen chloride or trifluoro acetic acid in a protic solvent.

Alternately, compounds of the invention IA may be obtained by the route depicted in Scheme II (where x is 0 or 1).

Reaction Scheme II

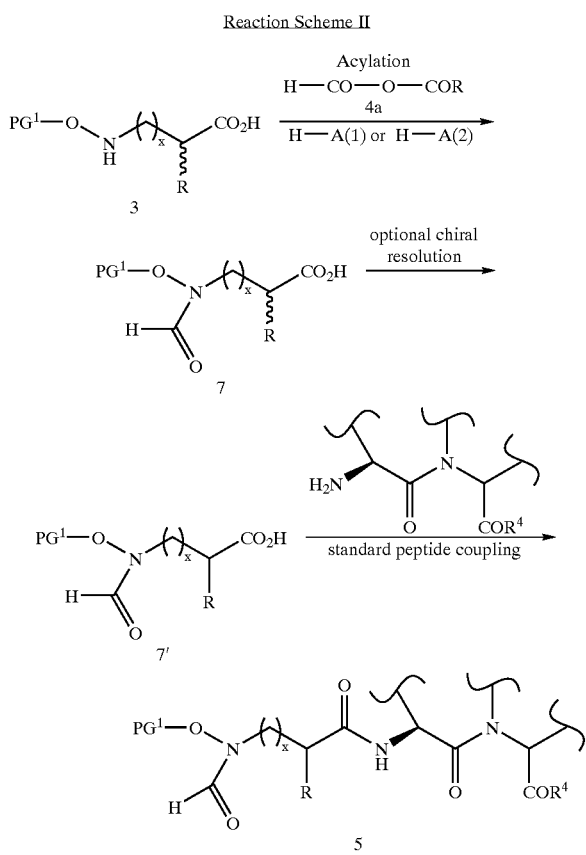

As seen in Reaction Scheme II, compound 3 may be formylated with a formylating agent 4a to give acid compound 7. This acid may be coupled with A(1) or A(2) directly or optically resolved to give 7* and then coupled to give compound 5. Compound 5 is then converted to compound of the invention IA as described above.

The compounds of formula I of the invention contain one or more asymmetric centers. Thus, these compounds can exist in diastereoisomeric forms or in mixtures thereof and all of such forms are within the scope of this invention. The above described processes can utilize racemates, enantiomers, or diastereomers as starting materials. When diastereomeric compounds are prepared, they can be separated by conventional chromatographic or fractional crystallization methods.

The compounds of formula I of the invention can be isolated in the form of a pharmaceutically acceptable salt. Suitable salts for this purpose are alkali metal salts such as sodium and potassium, alkaline earth metal salts such as calcium and magnesium, and salts derived from amino acids such as arginine, lysine, etc. These salts are obtained by reacting the acid form of the compound with an equivalent of base supplying the desired ion in a medium in which the salt precipitates or in aqueous medium and then lyophilizing.

The compounds of formula I of the invention are inhibitors of angiotensin converting enzyme and/or neutral endopeptidase. Thus, the compounds of formula I including their pharmaceutically acceptable salts are useful in the treatment of physiological conditions in which either angiotensin converting enzyme inhibitors or neutral endopeptidase inhibitors have been shown to be useful. Such conditions include cardiovascular diseases, particularly, hypertension, congestive heart failure, renal failure, and hepatic cirrhosis, as well as analgesic activity. The compounds of formula I are also inhibitors of other metalloproteases such as the matrix metalloproteases, for example, gelatinase, collagenase and stromylysin and thus are useful in the treatment of osteoarthritis, rheumatoid arthritis, metastatic tumors, and angiogenesis.

Diuresis, natriuresis, and blood pressure reduction are produced in a mammalian host such as man by the administration of from about 1 mg. to about 100 mg. per kg. of body weight per day, preferably from about 1 mg. to about 50 mg. per kg. of body weight per day, of one or more of the compounds of formula I or a pharmaceutically acceptable salt thereof. The compounds of formula I are preferably administered orally, but parenteral routes such as subcutaneous, intramuscular, and intravenous can also be employed. The daily dose can be administered singly or can be divided into two to four doses administered throughout the day.

The ACE and/or NEP inhibitors of formula I can be administered in combination with human ANF 99–126. Such combination would contain the inhibitor of formula I at from about 1 to about 100 mg. per kg of body weight and the human ANF 99–126 at from about 0.001 to about 0.1 mg. per kg. of body weight.

The ACE and/or NEP inhibitors of formula I can be administered in combination with other classes of pharmaceutically active compounds. For example, a calcium channel blocker, a potassium channel activator, a cholesterol reducing agent, etc.

The ACE and/or NEP inhibitors of formula I or a pharmaceutically acceptable salt thereof and other pharmaceutically acceptable ingredients can be formulated for the above described pharmacetical uses. Suitable compositions for oral administration include tablets, capsules, and elixirs, and suitable compositions for parenteral administration include sterile solutions and suspensions. About 10 to 500 mg. of active ingredient is compounded with physiologically acceptable vehicle, carrier, excipient, binder, preservative, stabilizer, flavoring, etc., in a unit dose form as called for by accepted pharmaceutical practice.

Preferred compounds of the invention are those of formula I wherein $R^1$ is H, x is 1, R is alkyl or arylalkyl, and A is A(1), preferably where

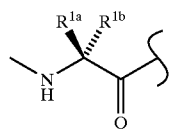

is preferably a non-proteinogenic amino acid portion wherein, $R^{1a}$ and $R^{1b}$ are each independently alkyl such as methyl or ethyl, or arylalkyl such as benzyl, or $R^{1a}$ and $R^{1b}$ together with the carbon to which they are attached form a 3–7 membered ring, preferably a 5-membered ring, or $R^{1a}$ and/or $R^{1b}$ is biphenylmethylene and the other may be H.

Also preferred are compounds where A is A(1), preferably where

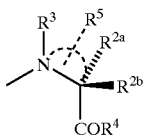

and is a non-proteinogenic amino acid where $R^3$ is H, alkyl, such as methyl or ethyl, aryl such as phenyl, or arylalkyl, such as benzyl, $R^{2a}$ and $R^{2b}$ are independently selected from H, alkyl, aryl, arylalkyl (with at least one of $R^{2a}$ and $R^{2b}$ being other than H) or $R^{2a}$ and $R^{2b}$ together with the carbon to which they are attached form a 3–7 membered ring, preferably 5- or 6-membered ring.

Also preferred are compounds where A is A(2) wherein $R^4$ is OH.

The following Examples represent preferred embodiments of the present invention.

EXAMPLE 1

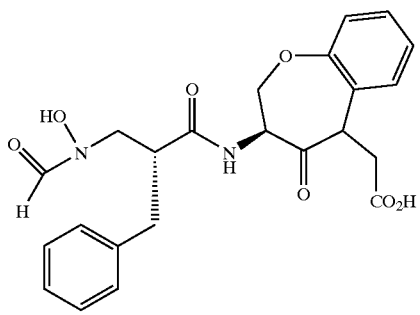

A.

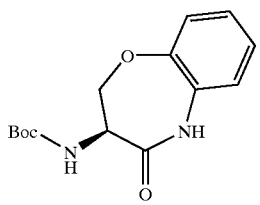

A(1).

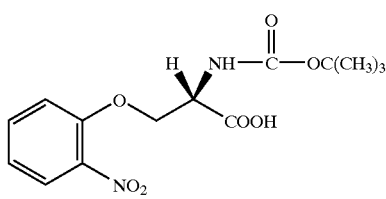

A solution of BOC-L-serine (24.3 g, 0.118 mole) in dry dimethylformamide (25 ml) was added dropwise over a period of 1.0 hour to a cooled (0°, ice-salt bath) suspension of 60% NaH (10.1 g, 0.25 mole) in dry dimethylformamide (200 ml) and stirring was continued at 0° until the frothing subsided (ca. 2.0 hours). The reaction mixture was treated dropwise with 1-fluoro-2-nitrobenzene (14.3 ml, 0.13 mole) over a period of 20 minutes, stirred at 0° under argon for 4.0 hours then poured into ice-water (750 ml) and extracted with $Et_2O$ (2×100 ml). The aqueous phase was brought to pH 1.0 with 6 N HCl (70 ml), extracted with EtOAc (3×500 ml) and the combined organic extracts were washed with brine (100 ml), dried (anhydrous $Na_2SO_4$), filtered, evaporated to dryness and dried in vacuo. The crude product mixture was chromatographed on a silica gel column (Merck), eluting the column with $CH_2Cl_2:CH_3OH:HOAc$ (100:5:0.2) to give title compound as a thick yellow syrup (27.222 g, 70.7%) with consistent $^1$H-NMR and $^{13}$C-NMR spectral data. TLC: $R_f$ 0.27 (Silica gel; $CH_2Cl_2:CH_3OH:HOAc$—100:5:0.5; UV, PMA).

A(2).

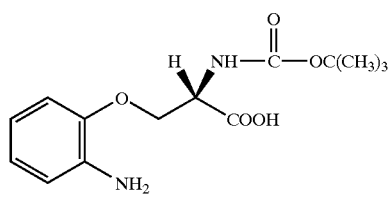

A solution of Part A(1) compound (27.1 g, 83 mmoles) in dry methanol (500 ml) was treated with 10% Pd/C (900 mg) and hydrogenated at 40 psi for 2.0 hours. The reaction mixture was filtered through a Celite® pad in a millipore unit, washing the pad well with $CH_3OH$ (5×100 ml). The dark filtrate was evaporated to dryness and dried in vacuo to give a dark solid. The crude product was triturated with $CH_2Cl_2$:Hexane (1:4) to give title compound as a light tan solid (17.69 g, 71. %) with consistent $^1$H-NMR and $^{13}$C-NMR spectral data. TLC: $R_f$ 0.15 (Silica gel; $CH_2Cl_2:CH_3OH:HOAc$—20:1:1; UV).

A(3).

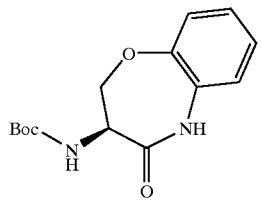

A solution of Part A(2) compound (16.69 g, 56.3 mmoles) in dry dimethyformamide (121 ml) was treated with 1-ethyl-3-(3-dimethylaminopropyl)carbodiimide (10.64 g, 55.5 mmoles) and stirred at room temperature for 3.0 hours. The reaction mixture was partitioned between EtOAc (2×492 ml) and 1.0 N $NaHCO_3$ (492 ml), and the combined organic extracts were washed with $H_2O$ (3×492 ml), brine (492 ml), dried (anhydrous $MgSO_4$), filtered, evaporated to dryness and dried in vacuo. The crude product was chromatographed on a silica gel column (Merck), eluting the column with EtOAc:Hexane mixtures (1:4; 1:2; 1:1) to give title compound as off-white crystals (10.5 g, 72.4%) with consistent $^1$H-NMR and $^{13}$C-NMR spectral data. TLC: $R_f$ 0.40 (Silica gel; EtOAc:Hexane—1:4; UV).

B.

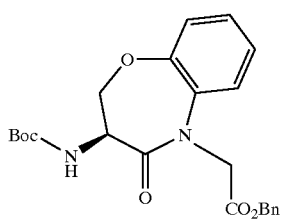

A solution of Part A compound (640 mg, 2.30 mmol) in dry THF (12 mL) at 0° C. was treated with LiN(TMS)$_2$ (1.0 M in THF, 2.60 mL, 2.60 mmol) followed approximately 30 seconds later with benzyl bromoacetate (475 μL, 687 mg, 3.0 mmol). After 25 minutes, the mixture was quenched with saturated NH$_4$Cl, diluted with H$_2$O, and extracted with EtOAc. The EtOAc extract was washed with H$_2$O and brine, then dried (Na$_2$SO$_4$), filtered and stripped to give a yellow oil. Flash chromatography (Merck SiO$_2$, 3/7-EtOAc/hexanes as eluant) provided title compound (967 mg, 98%) as a colorless oil/foam.

C.

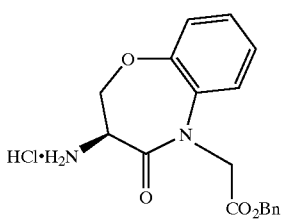

A solution of Part B compound (960 mg, 2.25 mmol) in 1,4-dioxane (4 mL) was treated with a solution of 4.0 M HCl in 1,4-dioxane (6 mL) at room temperature. After 3 hours, the mixture was concentrated in vacuo, triturated with Et$_2$O to give a solid and stripped to afford title compound (858 mg, 105% of theory).

m.p. 152–155° C.

D.

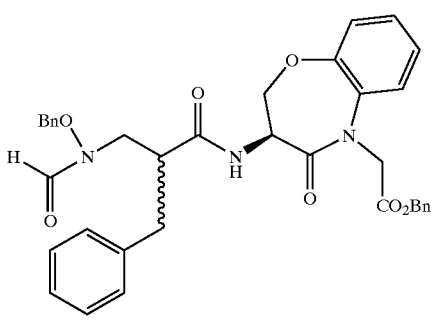

D(1).

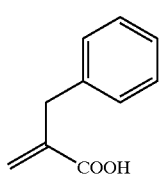

A solution of benzylmalonic acid (23.06 g, 0.12 mole) in H$_2$O (200 mL) was treated with 37% CH$_2$O solution (278.4 mL) and 40% aqueous (CH$_3$)$_2$NH (35 mL, 0.31 mole) then stirred overnight at room temperature under argon. The clear solution was heated to an internal temperature of 90° C. for 2.0 hours (at which time gas evolution had ceased), cooled and acidified to pH 1.0 with 12 N HCl (20 mL). The white precipitates were filtered off, washed with H$_2$O (3×25 mL) and dried in vacuo to give title compound as a white solid (12.85 g, 66.6%) with consistent $^1$H-NMR and $^{13}$C-NMR spectral data. TLC: R$_f$ 0.63 (Silica gel; CH$_2$Cl$_2$:MeOH—9:1; UV). m.p. 66–68° C.

D(2).

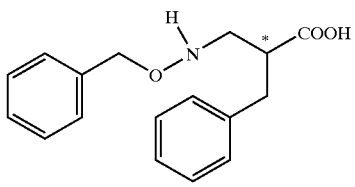

(J. Med. Chem. 28, 1985, 1167)

A solution of Part D(1) compound (8.9 g, 54.9 mmoles) and O-benzylhydroxylamine (26.7 g, 0.23 mole) in absolute EtOH (9.0 ml) was refluxed for 7 days, cooled to room temperature and evaporated to dryness. The residual syrup was dissolved in 1.0 N NaOH (55 ml), stirred for 15 minutes then extracted with EtOAc (4×18 ml). The organic phase was washed with H$_2$O (3×10 ml) and the aqueous extracts were combined and acidified to pH 2.0 with 1.0 N HCl (62 ml). The acidic aqueous phase was then extracted with EtOAc (5×75 ml) and the combined organic extracts washed with H$_2$O (2×30 ml), dried (anhydrous Na$_2$SO$_4$), filtered, evaporated to dryness and dried in vacuo. The crude product (3.93 g, 25.1%) was triturated with Et$_2$O:Hexane (1:4; 2×25 ml) and all solids obtained were dissolved in CH$_2$Cl$_2$ and filtered, washing the insoluble precipitates with CH$_2$Cl$_2$. The clear filtrate was evaporated and dried in vacuo to give title compound as an opaque colorless solid with consistent $^1$H-NMR and $^{13}$C-NMR spectral data.

TLC: R$_f$ 0.33 (Silica gel; CH$_2$Cl$_2$:MeOH—9:1; UV, PMA).

M.p. 69–71° C.

D(3).

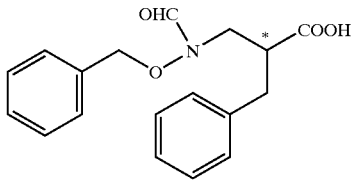

A cooled (0° C., ice-salt bath) mixture of HCOOH (17.5 ml) and acetic anhydride (Ac$_2$O) (1.75 ml) was stirred for 20 minutes, treated with Part D(2) compound (1.0 g, 3.5 mmoles) and stirring was continued at 0° C. for another 3.0 hours. The reaction mixture was stripped to dryness, evaporated from Et$_2$O (2×25 ml), toluene (20 ml) and hexane (2×50 ml) then dried in vacuo to give title compound as a thick syrup (1.096 g, 100% crude yield) with consistent $^1$H-NMR and $^{13}$C-NMR spectral data. TLC: R$_f$ 0.23 (Silica gel; CH$_2$Cl$_2$:MeOH—9:1; UV, PMA).

D(4).

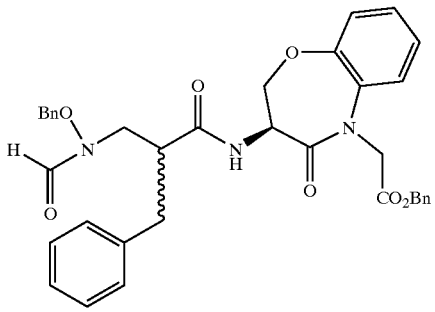

A solution of Part D(3) compound (366 mg, 1.19 mmol) in CH$_2$Cl$_2$ (9 mL) at 0° C. was treated with HOBT hydrate (210 mg) followed by EDAC (230 mg, 1.20 mmol). After 20 minutes, the mixture was treated with Part C amine hydrochloride 3 (390 mg, 1.07 mmol) followed by 4-methylmorpholine (200 μL, 184 mg, 1.8 mmol). The mixture was stirred at 0° C. for 1 hour and at room temperature for 2 hours. The reaction was partitioned between EtOAc and 5% KHSO$_4$. The EtOAc extract was washed successively with H$_2$O, 50% saturated NaHCO$_3$ and brine, then dried (Na$_2$SO$_4$), filtered and stripped. Flash chromatography (Merck SiO$_2$, 50% to 60% EtOAc in hexanes as eluant) provided title compound (550 mg, 84%) as a white foam which was shown by NMR and HPLC to be a 1:1 mixture of diastereomers.

E.

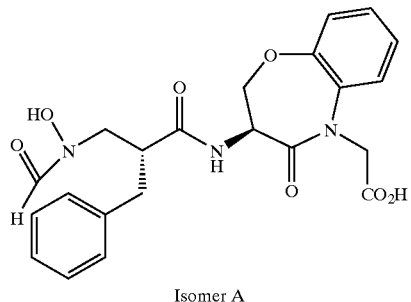

Isomer A

A solution of Part D compound (535 mg, 0.87 mmol) in MeOH (10 mL) was hydrogenated (balloon) over 10% Pd/C (123 mg) at room temperature for 2.75 hours. The solvent was filtered through Celite and the filtrate was stripped to give a diastereomeric mixture of title Isomer A and Isomer B

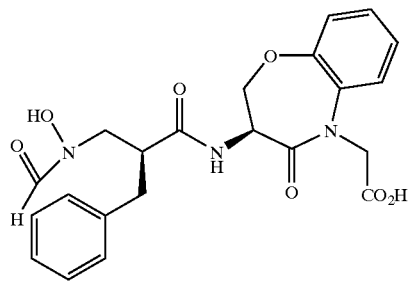

Isomer B

Trituration of a solution of the residue in MeOH with Et$_2$O provided 350 mg of the diastereomeric mixture. Approximately 255 mg of this mixture was separated by preparative HPLC (YMC S5 ODS 30×250 mm column; flow rate 25 mL/min detecting at 220 nm; 40 to 100% B over a 30 minute linear gradient (solvent A: 90% H$_2$O-10% MeOH-0.1% TFA; solvent B: 10% H2O-90% MeOH-0.1% TFA); title Isomer A t$_R$=14.4 min; separation performed in three runs). The desired fractions were stripped, azetroped with EtOAc, re-dissolved in EtOAc and triturated with Et$_2$O to give title Isomer A (105.5 mg) as an off-white solid.

MS: (M+NH$_4$)$^+$ 459; (M−H)$^-$ 440

HPLC YMC S3 ODS column (6.0×150 mm); eluted with B:A solvent mixture, 40 to 100% B over a 20 minute linear gradient (solvent A: 90% H2O-10% MeOH-0.2% H$_3$PO$_4$; solvent B: 0% H2O-90% MeOH-0.2% H$_3$PO$_4$); flow rate 1.5 mL/min detecting at 220 nm; t$_R$=9.67 min (96.0%).

Anal. Calc'd for C$_{22}$H$_{23}$N$_3$O$_7$·1.6H$_2$O·0.1EtOAc·0.1Et$_2$O C, 56.29; H, 5.80; N, 8.64. Found: C, 56.21; H, 5.15; N, 8.29.

EXAMPLE 2

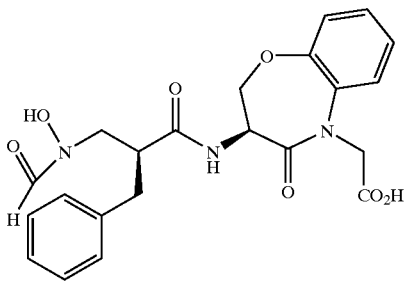

A solution of Example 1 Part E Isomers A and B (1:1 mixture of diastereomers, 535 mg, 0.87 mmol) in MeOH (10 mL) was hydrogenated (balloon) over 10% Pd/C (123 mg) at room temperature for 2.75 hours. The solvent was filtered through Celite and the filtrate was stripped to give a diastereomeric mixture of Isomers A and B. Trituration of a solution of the residue in MeOH with Et$_2$O provided 350 mg of the diastereomeric mixture. Approximately 255 mg of this mixture was separated by preparative HPLC (YMC S5 ODS 30×250 mm column; flow rate 25 mL/min detecting at 220 nm; 40 to 100% B over a 30 minute linear gradient (solvent A: 90% H$_2$O-10% MeOH-0.1% TFA; solvent B: 10% H$_2$O-90% MeOH-0.1% TFA); Isomer B t$_R$=18.6 min; separation performed in three runs). The desired fractions were stripped, azetroped with EtOAc, re-dissolved in EtOAc and triturated with Et$_2$O to give Isomer B (88.0 mg) as an off-white solid.

MS: (M+NH$_4$)$^+$ 459; (M−H)$^-$ 440.

HPLC YMC S3 ODS column (6.0×150 mm); eluted with B:A solvent mixture, 40 to 100% B over a 20 minute linear gradient (solvent A: 90% H$_2$O-10% MeOH-0.2% H$_3$PO$_4$; solvent B: 0% H$_2$O-90% MeOH-0.2% H$_3$PO$_4$); flow rate 1.5 mL/min detecting at 220 nm; t$_R$=13.8 min (94.0%).

Anal. Calc'd for C$_{22}$H$_{23}$N$_3$O$_7$·1.5H$_2$O·0.2Et$_2$O C, 56.66; H, 5.84; N, 8.69. Found: C, 56.84; H, 5.22; N, 8.42.

EXAMPLE 3

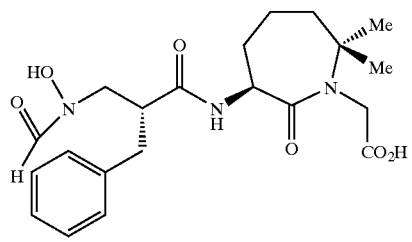

A.

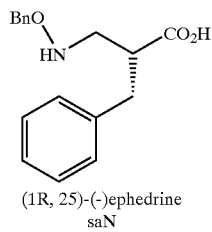

(1R, 2S)-(-)-ephedrine
saN

A solution of Example 1 Part D(1) compound

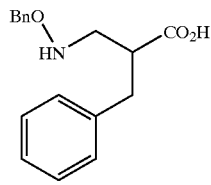

(2.563 gm, 8.98 mmol) in CH$_3$CN (20 mL) was treated with (1R,2S)-(-)-ephedrine (1.522 gm, 9.2 mmol) and stirred until homogeneous. Most of the solvent was removed by rotary evaporation and the residue was dissolved in Et$_2$O (25 mL) and treated with hexane (16 mL) in portions until the mixture was slightly turbid. The solution was seeded and let stand overnight at room temperature. The precipitate was collected by filtration and rinsed with 1:1 Et$_2$O:hexanes and dried to afford 2.101 gm of white crystals ([a]$_D$=-16.4° (c 0.6, CH$_2$Cl$_2$)). The solid (2.087 gm) was dissolved in CH$_2$Cl$_2$, concentrated and diluted with Et$_2$O (18 mL) and hexane (8 mL) and seeded. The precipitate was collected by filtration and washed with 1:1-Et$_2$O:hexanes followed by hexanes to give title compound (1.995 gm) which was diastereomerically enriched in one isomer but not diastereomerically pure ([a]$_D$=-17.0° (c 0.6, CH$_2$Cl$_2$)).

mp 110–114° C.

Material suitable for x-ray crystallographic analysis was obtained by repeated recrystallization of the solid from CH$_3$CN. mp 117–119° C.; ([α]$_D$=-19.7° (c 0.4, CH$_2$Cl$_2$)).

B.

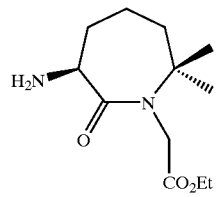

B(1).

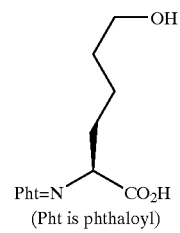

(Pht is phthaloyl)

To a stirred solution of L-(+)-hydroxynorleucine (75 g, 509.6 mmole) and sodium carbonate (54 g, 509.6 mmole) in water (900 ml) at room temperature under argon was treated with N-ethoxy-carbonyl-phthalimide (111.7 g, 509.6 mmole). After being stirred for 2.0 hours, the resulting solution was filtered through a pad of celite. The filtrate was cooled in an ice bath and carefully acidified to pH=3 with 6N HCl solution. The white solid which had precipitated was filtered and dried over P$_2$O$_5$ in vacuo to afford Compound 1 (124.5 g) in 88.1% yield.

M.P. 162° C.

H$^1$-NMR (DMSO): d=1.32 (m, 6H), 2.13 (m, 2H), 4.38 (s, OH), 5.75 (m, 1H), 7.92 (m, 4H) ppm.

B(2).

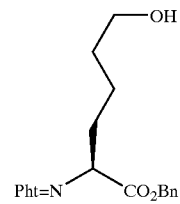

To a stirred slurry of Part B(1) compound (124.5 g, 0.449 mole) and cesium carbonate (73.2 g, 0.225 mole) in DMF (1.25 L) at room temperature under argon was added benzyl bromide (98.4 g, 0.575 mole). After 2.5 hours, the resulting solution was poured into EtOAc (3.0 L), washed with water (3×), 5% LiCl solution and brine, dried over anhydrous Mg$_2$SO$_4$ and evaporated in vacuo to afford title compound (142 g) as an oil in 86.1% yield.

H$^1$-NMR (CDCl$_3$): d=1.50 (m, 4H), 2.32 (m, 2H), 3.62 (m, 2H), 4.91 (dd, 1H), 5.22 (d, 2H), 7.31 (m, 5H), 7.77 (m, 2H), 7.86 (m, 2H) ppm.

C$^{13}$-NMR (CDCl$_3$): 22.62, 28.46, 31.91, 52.32, 62.32, 67.46, 123.55, 128.06, 128.31, 128.53, 131.77, 134.23, 135.28, 167.76, 169.25 ppm.

B(3).

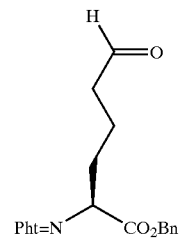

To a stirred and chilled (-78° C., Dry ice-IPA bath) oxalyl chloride solution (2.0 M solution in CH$_2$Cl$_2$, 16.3 ml, 32.6 mmole) under argon was added dropwise a solution of dimethyl sulfoxide (4.64 ml, 65.32 mmole) in dry CH$_2$Cl$_2$ (10 ml). After the addition was complete, the solution was stirred at −78° for 15 minutes, then treated with a solution of Part B(2) compound (10 g, 27.22 mmole) in dry CH₂Cl₂ (70 ml), stirred at −78° for another 15 minutes and slowly treated with triethylamine (16 ml). The resulting solution was stirred at −78° for 15 minutes, gradually warmed up to 0°, poured into 1:1 EtOAc-Et₂O (500 ml), washed with 1.0 N HCl solution, water and brine, dried over anhydrous Mg₂SO₄ and evaporated in vacuo to afford title compound (10 g) as a light yellow oil in 100% yield.

H¹-NMR (CDCl₃): d=1.66 (m, 2H), 2.40 (m, 4H), 4.90 (dd, 1H), 5.18 (d, 2H), 7.35 (m, 5H), 7.74 (m, 2H), 7.86 (m, 2H), 9.72 (s, 1H) ppm.

C¹³-NMR (CDCl₃): 18.66, 27.99, 42.87, 51.83, 67.47, 123.50, 128.00, 128.26, 128.44, 131.58, 134.21, 135.04, 167.55, 168.80, 201.31 ppm.

B(4).

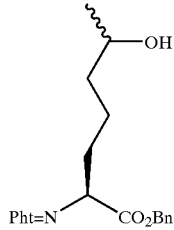

A stirred and chilled (0° C., ice bath) solution of Part B(3) compound (10.1 g, 27.64 mmole) in dry CH₂Cl₂ (100 ml) under argon was treated with a solution of trimethylaluminum (2.0 M solution in hexane, 23.4 ml, 46.8 mmole). The resulting solution was stirred for 45 minutes, quenched with 100 ml of a saturated NH₄Cl solution (foaming) and partitioned between 1:1 Et₂O-water (400 ml). The organic layer was separated and the aqueous layer was re-extracted with EtOAc (2×150 ml). The organic extracts were combined, washed with brine, dried over anhydrous Mg₂SO₄ and evaporated in vacuo to afford title compound (10.3 g) as a gum in 98.7% yield.

TLC: Silica gel, 6:4 EtOAc-hexane, R_f=0.42, UV and PMA.

H¹-NMR (CDCl₃): d=1.12 (d, 3H), 1.43 (m, 4H), 3.73 (m, 2H), 4.90 (dd, 1H), 5.19 (d, 2H), 7.30 (m, 5H), 7.76 (m, 2H), 7.86 (m, 2H) ppm.

C¹³-NMR (CDCl₃): 22.5, 23.40, 28.47, 28.59, 38.20, 38.34, 52.20.67.35, 67.51, 123.43, 127.94, 128.19, 128.41, 131.65, 134.11, 135.16, 167.62, 167.67, 169.13 ppm.

B(5).

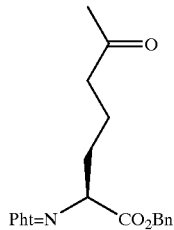

To a stirred and chilled (−78° C., Dry ice-IPA bath) oxalyl chloride solution (2.0 M solution in CH₂Cl₂, 257.3 ml, 514.6 mmole) under argon was added CH₂Cl₂ (300 ml). To this solution, a solution of dimethyl sulfoxide (80.4 g, 1.03 mole) in dry CH₂Cl₂ (30 ml) was added dropwise. After the addition was complete, the reaction mixture was stirred at −78° for 20 minutes, treated with a solution of Part B(4) compound (151 g, 395.88 mmole) in dry CH₂Cl₂ (700 ml), stirred at −78° C. for another 20 minutes and slowly treated with triethylamine (300 ml). The resulting solution was stirred at −78° for 15 minutes, gradually warmed up to 0°, poured into 1:1 EtOAc-Et₂O (3 L), washed with 1.0 N HCl solution, water and brine, dried over anhydrous Mg₂SO₄ and evaporated in vacuo to afford title compound (149.4 g) as a yellow oil in 99.5% yield.

TLC: Silica gel, 6:4 EtOAc-hexane, R_f=0.5, UV and PMA.

H¹-NMR (CDCl₃): d=1.60 (m, 2H), 2.10 (s, 3H), 2.26 (m, 2H), 2.47 (m, 2H), 4.90 (dd, 1H), 5.19 (d, 2H), 7.30 (m, 5H), 7.74 (m, 2H), 7.84 (m, 2H) ppm.

C¹³-NMR (CDCl₃): 20.15, 27.93, 29.84, 42.47, 51.89, 67.40, 123.46, 127.97, 128.23, 128.43, 131,61, 134.17, 135.10, 167.57, 168.93, 207.80 ppm.

B(6).

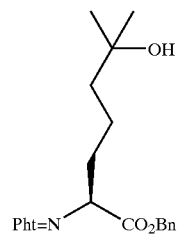

A chilled (−78° C. Dry ice-IPA Bath) and stirred solution of titanium(IV) chloride (112.05 g, 590.65 mmole) in CH₂Cl₂ (1.5 L) under argon was treated with methylmagnesium chloride (3 M solution in THF, 196.9 ml, 590.65 mmole). The black solution was allowed to warm up to −35° C. and a solution of Part B(5) compound (149.4 g, 393.77 mmole) was added dropwise. After the addition was complete, the resulting solution was allowed to warm up to 0° C., stirred at 0° C. for 2 hours and quenched with saturated NH₄Cl solution. The CH₂Cl₂ layer was separated. The aqueous layer was extracted with CH₂Cl₂ (2×700 ml). The CH₂Cl₂ extracts were combined, washed with brine, dried over anhydrous Mg₂SO₄ and evaporated in vacuo. The black residue was passed through a pad of silica gel (E. Merck, 230–400 mesh, 900 g) eluting with EtOAc-hexane (1:1) to afford a tlc-homogeneous title compound (144.8 g) as a yellow oil in 93% in yield.

TLC: Silica gel, 1:1 EtOAc-hexane, R_f=0.4, UV and PMA.

H¹-NMR (CDCl₃): d=1.14 (s, 6H), 1.45 (m, 4H), 2.30 (m, 2H), 4.90 (dd, 1H), 5.19 (d, 2H), 7.30 (m, 5H), 7.74 (m, 2H), 7.86 (m, 2H) ppm.

C¹³-NMR (CDCl₃): 20.88, 29.00, 29.17, 42.78, 52.13, 67.35, 70.47, 123.44, 127.95, 128.19, 128.41, 131.66, 134.11, 167.66, 169.14 ppm.

B(7).

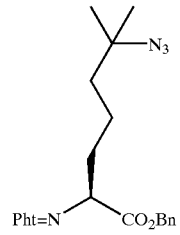

A stirred solution of Part B(6) compound (44.3 g, 364.89 mmole) and azidotrimethylsilane (63.06 g, 547.34 mmole) in dry CH₂Cl₂ (2.2 L) at room temperature under argon was treated with boron trifluoride diethyl etherate (67.32 g, 474.36 mmole). After being stirred for 5 days, the resulting solution was quenched with water (1.5 L). The organic layer was separated, washed with saturated NaHCO$_3$ solution, water and brine, dried over anhydrous Mg$_2$SO$_4$ and evaporated in vacuo. The residue was chromatographed on a column of silica gel (E. Merck, 230–400 mesh, 700 g) eluting with EtOAc-hexane (1:3) to afford a tlc-homogeneous title compound (124.9 g) as a light yellow oil in 81.3% yield.

TLC: Silica gel, 3:7 EtOAc-hexane, R$_f$=0.5, UV and PMA.

H$^1$-NMR (CDCl$_3$): d=1.20 (s, 6H), 1.45 (m, 4H), 2.30 (m, 2H), 4.90 (dd, 1H), 5.19 (d, 2H), 7.30 (m, 5H), 7.74 (m, 2H), 7.86 (m, 2H) ppm.

C$^{13}$-NMR (CDCl$_3$): 20.97, 25.67, 25.92, 28.80, 40.53, 52.02, 61.16, 67.40, 123.47, 127.97, 128.23, 128.43, 131.66, 134.14, 135.12, 167.60, 169.01 ppm.

B(8).

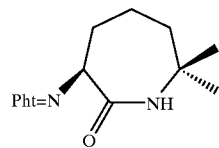

A solution of Part B(7) compound (124.8 g, 296.81 mmole) and 10% Pd/C (32 g) in dry DMF (2.0 L) was hydrogenated for 24 hours. After completion, argon was bubbled through the reaction mixture to remove excess hydrogen and methyl sulfide (2.6 ml) was added to poison the palladium. To this solution 1-hydroxybenzotriazole hydrate (46.74 g) was added and followed by ethyl-3(3-dimethylamino)propylcarbodiimide hydrochloride salt (68.74 g). The resulting solution was stirred at room temperature under argon for 3.5 hours, diluted with EtOAc (2 L) and filtered through a pad of celite. The filtrate was washed with 0.5 N HCl solution, saturated NaHCO$_3$ solution, and brine, dried over anhydrous Mg$_2$SO$_4$ and evaporated in vacuo to give a gum. This was triturated with Et$_2$O-hexane (2:1) to afford a tlc-homogeneous title compound (74.5 g) as a white solid in 87.7% yield.

TLC: Silica gel, 3:7 EtOAc-CH$_2$Cl$_2$, R$_f$=0.35, UV and PMA.

H$^1$-NMR (CDCl$_3$): d=1.30 (s, 3H), 1.45 (s, 3H), 1.74 (m, 2H), 1.96 (m, 3H), 2.74 (m, 1H), 4.98 (d, 1H), 6.00 (s, 1H), 7.20 (m, 2H), 7.85 (m, 2H) ppm.

C$^{13}$-NMR (CDCl$_3$): 23.89, 26.65, 29.58, 33.32, 40.68, 52.69, 54.51, 123.34, 123.15, 133.87, 168.06, 171.03 ppm.

B(9).

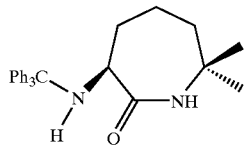

A stirred solution of Part B(8) compound (74.5 g, 260.19 mmole) in a mixture of CH$_3$OH (900 ml) and CH$_2$Cl$_2$ (250 ml) at room temperature under argon was treated with hydrazine monohydrate (18.24 g, 364.26 mmole). After 48 hours, the solid was filtered off and the filtrate was evaporated in vacuo to give a solid (41 g).

To a stirred solution of the above solid (41 g) in CH$_2$Cl$_2$ (2 L) at room temperature under argon was added triethylamine (50 ml) and triphenylmethyl chloride (83.41 g). After 1.5 hours, the resulting slurry was diluted with EtOAc, washed with water and brine, dried over anhydrous Mg$_2$SO$_4$ and evaporated in vacuo to give a gum. This was triturated with Et$_2$O-pentane to give title compound (100.1 g) as a white solid in 96.5% yield.

TLC: Silica gel, 6:4 EtOAc-hexane, R$_f$=0.53, UV and PMA.

H$^1$-NMR (CDCl$_3$): d=1.00 (s, 3H), 1.10 (s, 3H); 1.46 (m, 6H), 3.36 (m, 1H), 4.03 (m, 1H), 5.20 (d, 1H), 6.00 (s, 1H), 7.20 (m, 2H), 7.85 (m, 2H) ppm.

C$^{13}$-NMR (CDCl$_3$): 22.86, 25.81, 33.50, 34.23, 40.16, 51.97, 55.60, 71.89. 126.22, 127.61, 128.96, 146.48, 176.71 ppm.

B(10).

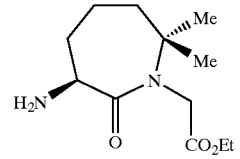

To a stirred solution of Part B(9) compound (50 g, 125 mmole) in dry THF (1020 ml) at room temperature under argon was added simultaneously (at same rate) a solution of lithium bis(trimethylsily)amide (1.0 M solution in THF, 627.3 ml, 627.3 mmole) and a solution of ethyl bromoacetate (104.8 g, 627.3 mmole) in THF (523 ml) over the period of 1.0 hour. After the addition was complete, the solution was stirred for 30 hours, quenched with saturated NH$_4$Cl solution (1.0 liter) and extracted with EtOAc (3×700 ml). The EtOAc extracts were combined, washed with saturated NaHCO$_3$ solution and brine, dried over anhydrous Mg$_2$SO$_4$ and evaporated in vacuo to afford a black oil. The experiment was repeated on the same scale to give a similar result. The combined black oils was chromatographed on a column of silica gel (E. Merck, 230–400 mesh, 1.6 kg) eluting with EtOAc-hexane (1:4) to give a light yellow oil. This was dissolved in dry CH$_2$Cl$_2$ (2 L) and treated with trifluoroacetic acid (78 ml). The solution was stirred at room temperature under argon for 1.0 hour and then evaporated in vacuo at 30°. The residue was diluted with 1.0 N HCl solution (400 ml) and washed with Et$_2$O (2×400 ml). The aqueous was carefully neutralized to pH=7–8 with solid NaHCO$_3$ (foaming) and extracted with CH$_2$Cl$_2$ (3×1.2 L). The CH$_2$Cl$_2$ extracts were combined, dried over anhydrous Na$_2$SO$_4$ and evaporated in vacuo to afford a tlc homogeneous title compound (51.5 g) as a light brown oil in 84.7% yield.

TLC: Silica gel, 8:1:1 CH$_2$Cl$_2$—CH$_3$OH-AcOH, R$_f$=0.3, PMA and Ninhydrin.

H$^1$-NMR (CDCl$_3$): d=1.28 (t, 3H), 1.36 (s, 3H), 1.38 (s, 3H) 1.60 (m, 1H), 1.90 (m, 5H), 3.75 (m, 1H), 4.00 (d, 1H), 4.22 (q, 2H), 4.28 (d, 2H) ppm.

C$^{13}$-NMR (CDCl$_3$): 14.00, 20.06, 28.19, 30.07, 32.29, 39.98, 46.87, 53.20, 58.38, 60.73, 170.35, 177,06 ppm.

C.

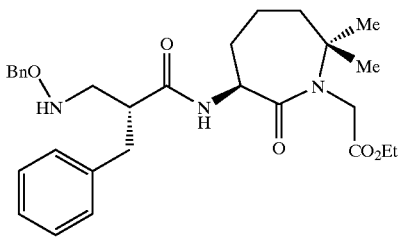

Part A compound (641 mg, 1.42 mmol) was partitioned between EtOAc and 5% $KH_2PO_4$ (adjusted to pH 2.5 with $H_3PO_4$). The layers were separated and the aqueous layer was back-extracted with EtOAc. The pooled EtOAc extracts were washed with brine, dried ($Na_2SO_4$), filtered and stripped to give an oil (assume 1.42 mg). The oil was dissolved in $CH_2Cl_2$ (10 mL) and the resulting solution was treated with Part B amine (364 mg, 1.50 mmol) in $CH_2Cl_2$ (2 mL) and cooled to 0° C. The mixture was subsequently treated with HOBT hydrate (195 mg) followed by EDAC (285 mg, 1.48 mmol). After stirring at 0° C. for 45 minutes and at room temperature for 45 minutes, the mixture was partitioned between EtOAc and 5% $KH_2PO_4$ (adjusted to pH 2.5 with $H_3PO_4$). The EtOAc extract was washed successively with $H_2O$, 50% saturated $NaHCO_3$ and brine, then dried ($Na_2SO_4$), filtered and stripped. The residue was flash chromatographed (Merck $SiO_2$, 7/3-EtOAc/hexanes as eluant) to obtain title compound (427 mg, 59%, TLC $R_f$ 0.37 (8/2-EtOAc/hexanes)) as a diastereomerically pure compound. In addition, the minor diastereomer was isolated from the column (66 mg, 9%, TLC $R_f$ 0.27 (8/2-EtOAc/hexanes)). NMR of this material was consistant with an isomer of the title compound.

D.

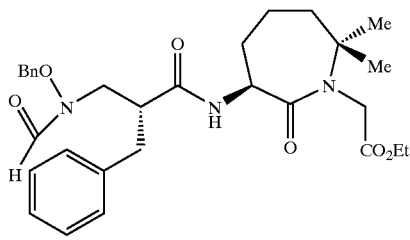

Acetic anhydride (500 μL) was added to formic acid (5.0 mL) at 0° C. and the mixture was stirred for 30 minutes. Approximately 2.6 mL of this solution was added to a solution of Part C compound (208 mg, 0.413 mmol) in THF (1.1 mL) at 0° C. After 30 minutes, most of the solvent was removed by rotary evaporation and the residue was partitioned between EtOAc and saturated $NaHCO_3$. The EtOAc extract was washed with brine, dried ($Na_2SO_4$), filtered and stripped to give title compound (216 mg, 97%) as an oily foam which was used directly in the next reaction without further purification.

TLC $R_f$ 0.37 (EtOAc).

HPLC YMC S3 ODS column (6.0×150 mm); eluted with B:A solvent mixture, 40 to 100% B over a 20 minute linear gradient (solvent A: 90% $H_2O$-10% MeOH-0.2% $H_3PO_4$; solvent B: 0% $H_2O$-90% MeOH-0.2% $H_3PO_4$); flow rate 1.5 mL/min detecting at 220 nm; $t_R$=17.2 min (100%).

E.

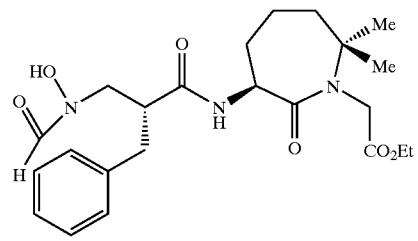

A solution of Part D compound (216 mg, 0.402 mmol) in absolute EtOH (5 mL) was hydrogenated (balloon) over 10% Pd/C (33 mg) at room temperature for 2 hours. The mixture was filtered through Celite, stripped, and azeotroped twice with EtOAc/$Et_2O$/hexanes to give title compound (174 mg, 97%) as an off-white foam.

TLC $R_f$ 0.33 (5/95-HOAc/EtOAc).

HPLC YMC S3 ODS column (6.0×150 mm); eluted with B:A solvent mixture, 40 to 100% B over a 20 minute linear gradient (solvent A: 90% $H_2O$-10% MeOH-0.2% $H_3PO_4$; solvent B: 0% $H_2O$-90% MeOH-0.2% $H_3PO_4$); flow rate 1.5 mL/min detecting at 220 nm; $t_R$=12.8 min (100%).

F.

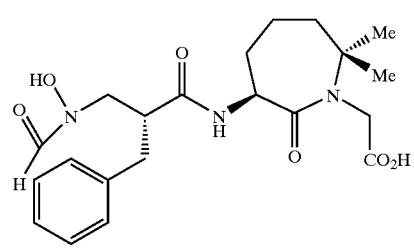

A stirred solution of Part E compound (168 mg, 0.376 mmol) in MeOH (3 mL) at room temperature was treated with aqueous 1 N NaOH (3 mL). An additional portion of aqueous 1 N NaOH (3 mL) was added after 3.5 hours. After a total of 6 hours, the mixture was made acidic with 5% $KHSO_4$ and extracted twice with EtOAc. The EtOAc extract was washed with brine, dried ($Na_2SO_4$), filtered and stripped. The residue was dissolved in a small amount of MeOH and EtOAc and triturated with $Et_2O$/hexanes to give title compound (134 mg, 86%) as an off-white solid/foam [[a]$_D$=+18.0° (c 0.5, $CH_2Cl_2$)].

TLC Rf 0.10 (5/95-HOAc/EtOAc).

HPLC YMC S3 ODS column (6.0×150 mm); eluted with B:A solvent mixture, 40 to 100% B over a 20 minute linear gradient (solvent A: 90% $H_2O$-10% MeOH-0.2% $H_3PO_4$; solvent B: 0% $H_2O$-90% MeOH-0.2% $H_3PO_4$); flow rate 1.5 mL/min detecting at 220 nm; $t_R$=9.00 min (>97.4%).

Anal. Calc'd for $C_{21}H_{29}N_3O_6 \cdot 0.75H_2O \cdot 0.3Et_2O$ C, 58.57; H, 7.42; N, 9.23. Found C, 58.31; H, 7.20; N, 8.99.

EXAMPLE 4

[S-(R*,R*)]-3-[[3-(Formylhydroxyamino)-1-oxo-2-(phenylmethyl)propyl]amino]-2,3,4,5-tetrahydro-2-oxo-1H-benzazepine-1-acetic acid

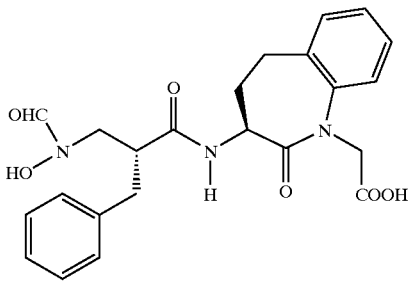

A.

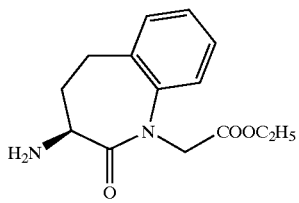

A(1).

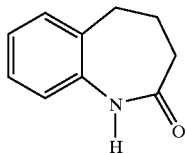

Solid sodium azide (26.0 g., 0.2 mole) was introduced into a 3-neck round-bottom flask with an overhead stirrer, made into a paste with warm water (26 ml), layered with chloroform (160 ml) and cooled down to 0° (ice-salt bath). The mixture was treated dropwise with concentrated sulfuric acid (11.2 ml, 0.5 eq.) over a period of 10 minutes, stirred for an additional 10 minutes then decanted into a flask containing anhydrous sodium sulfate. The dried solution was filtered through a glass wool plug in a funnel into a 500-ml round-bottom flask. Titration of an aliquot (1.0 ml) with 1.0 N NaOH using phenolphthalein as an indicator gave a normalitity of 1.7 N for the hydrazoic acid.

Tetralone (15.94 g, 0.108 mole) was added to the hydrazoic acid solution (0.136 mole or 1.25 eq.), heated to 40–45° (oil bath) then treated dropwise with 36.0 N $H_2SO_4$ (28.7 ml, 5 eq.) over a period of 1.0 hour. (Intense bubbling took place with each drop added for the first 30 minutes). The reaction mixture was cooled down to room temperature, poured into $H_2O$ (720 ml) and stirred for 5 minutes. The solution was then extracted with EtOAc (3×250 ml) and the combined organic extracts were washed with brine (100 ml), dried (anhydrous $MgSO_4$), filtered, evaporated to dryness and dried in vacuo. The crude product (17.819 g) was recrystallized from $CH_2Cl_2$ (70 ml) and Hexane (400 ml) to give title compound as off-white precipitates (10.017 g, m. pt. 138–140° C.) with consistent $^1H$-NMR and $^{13}C$-NMR spectral data.

The mother liquor was chromatographed on a silica gel column (Merck, 240 g), eluting the column with EtOAc:Hexane (1:4) to give an additional amount of 5.058 g (total yield=15.075 g, 85.6%).

TLC: $R_f$ 0.37 (Silica gel; EtOAc:Hexane—1:1; UV).

A(2).

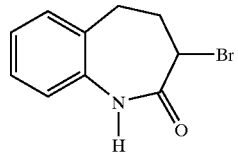

A solution of Part A(1) compound (1.0 g, 6.20 mmoles) in dry $CHCl_3$ (15 ml) was cooled down to 0° C. (ice-salt bath), treated with $PCl_5$ (1.5 g, 7.20 mmoles) followed by $I_2$ (15 mg) then stirred at 0° C. under argon for 30 minutes. The yellow solution was treated with $Br_2$ (0.39 ml or 1.2 g, 7.51 mmoles), warmed up to room temperature and refluxed under argon for 4.0 hours. The mixture was then poured into ice-water (20 g), stirred and the phases were separated, washing the aqueous phase with $CHCl_3$ (25 ml). The combined organic extracts were washed with $H_2O$ (5.0 ml), dried (anhydrous $MgSO_4$), filtered, evaporated to dryness and dried in vacuo. The crude product mixture was chromatographed on a silica gel column (Merck, 70 g), eluting the column with EtOAc:Hexane (1:9) to give title compound as off-white precipitates (1.137 g., m.pt. 170–172°, 70.1%) with consistent $^1H$-NMR and $^{13}C$-NMR spectral data.

TLC: $R_f$ 0.13 (Silica gel; EtOAc:Hexane—1:4; UV).

A(3).

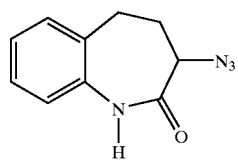

A solution of Part A(2) compound (936 mg, 3.9 mmoles) and $NaN_3$ (300 mg, 4.6 mmoles) in dry dimethylsulfoxide (20 ml) was stirred at 600 (oil bath) under argon for 6.0 hours. The reaction mixture was cooled down to room temperature, poured into cold water (125 ml), stirred for 15 minutes and filtered, washing the solids formed with water. The crude product was dried in vacuo at 60° over drierite for 24 hours to give title compound (725 mg, m.pt. 150–152°, 91.9%) as an off-white solid with consistent $^1H$-NMR and $^{13}C$-NMR spectral data.

TLC: $R_f$ 0.58 (Silica gel; EtOAc:Hexane—1:4 then 1:1; UV).

A(4).

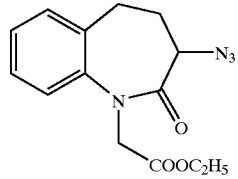

A solution of Part A(3) compound (10.858 g, 53.7 mmoles) in dry tetrahydrofuran (100 ml) was treated with $Bu_4NBr$ (1.791 g, 5.56 mmoles) and powdered KOH (3.937 g, 70.2 mmoles) followed by ethyl bromoacetate (6.8 ml, 61.3 mmoles). The reaction mixture was stirred at room temperature under argon for 1.5 hours then partitioned between H₂O (196 ml) and CH₂Cl₂ (2×375 ml). The combined organic extracts were washed with H₂O (2×196 ml) and brine (100 ml), dried (anhydrous Na₂SO₄), filtered, evaporated to dryness and dried in vacuo. The crude product was combined with the crude product mixture from a previous run (2.936 g, 12.86 mmole scale) and chromatographed on a silica gel column (Merck), eluting the column with Toluene:EtOAc (98.2) and EtOAc:Hexane (1:9) to give title compound as a solid (15.48 g, 93.5%)[1] with consistent ¹H-NMR and ¹³C-NMR spectral data.

TLC: $R_f$ 0.63 (Silica gel; EtOAc:Hexane—1:2; UV).

A(5).

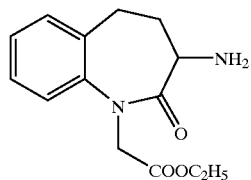

A solution of Part A(4) compound (8.95 g, 31.0 mmoles) in absolute ethanol (50 ml) was treated with 10% Pd/C (443 mg) and hydrogenated at 45 psi for 3.5 hours, venting the Parr bottle every 30 minutes for the first 1.5 hours. The mixture was filtered through a Celite® pad in a millipore unit, washing the pad well with absolute ethanol (3×50 ml). The clear filtrate was evaporated to dryness and dried in vacuo to give title compound as a thick yellow syrup (7.929 g, 97.5%) with consistent ¹H-NMR and ¹³C-NMR spectral data. TLC: $R_f$ 0.45 (Silica gel; CH₂Cl₂:CH₃OH—9:1; UV).

A(6).

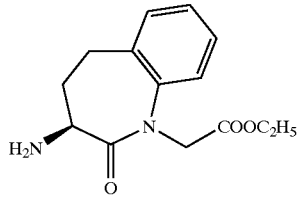

A solution of Part A(5) compound (14.8 g, 56.4 moles) and L-tartaric acid (8.50 g) in hot absolute ethanol (118 ml) was kept overnight at 0°, at room temperature for 3 days and then at 0° for another 2 days. The solid that formed was recrystallized from absolute ethanol (118 ml) two more times until a consistent specific rotation was obtained. The precipitates (6.319 g) from the second recrystallization was then suspended in EtOAc (100 ml), treated with 10% NH₄OH (12 ml) and stirred for 5 minutes. The organic phase was separated, washed with 10% NH₄OH (10 ml) and brine (15 ml), dried (anhydrous Na₂SO₄), filtered, evaporated to dryness and dried in vacuo to give title compound as a white solid (3.927 g, m.pt. 105–107°, 26.5%) with consistent ¹H-NMR and ¹³C-NMR spectral data.

$[a]_D$=−277° (c 0.99, EtOH). TLC: $R_f$ 0.45 (Silica gel; CH₂Cl₂:CH₃OH—9:1; UV).

B.

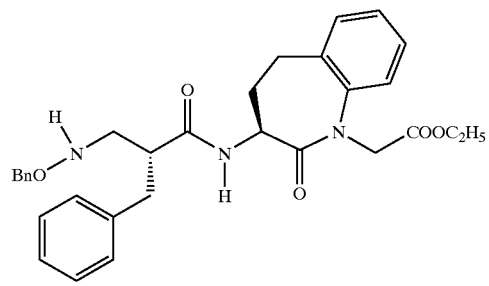

Example 3 Part A ephedrine salt (414 mg, 0.93 mmole), was partitioned between 5% KH₂PO₄ (adjusted to pH 2.5; 4.0 ml) and EtOAc (2×20 ml) and the combined organic extracts were washed with brine (4.0 ml), dried (anhydrous Na₂SO₄), filtered, evaporated to dryness and dried in vacuo to give the free acid of the Example 4 Part A compound as a clear syrup (286.6 mg, 100% crude yield).

A solution of the above free acid (286.6 mg, 0.93 mmole) in dry CH₂Cl₂ (6.0 ml) was cooled to 0° C. (ice-salt bath) and treated sequentially with a solution of the above free amine (271 mg) in dry CH₂Cl₂, HOBT.H₂O (126.1 mg, 0.93 mmole) and EDAC (185.4 mg, 0.97 mmole). The reaction mixture was stirred at 0° C. for 1.0 hour, at room temperature for 2.0 hours, then partitioned between EtOAc (2×20 ml) and H₂O (4.0 ml). The organic extracts were washed with 5% KH₂PO₄ (adjusted to pH 2.5; 4.0 ml), H₂O (4.0 ml), saturated NaHCO₃ (4.0 ml) and brine (4.0 ml), dried (anhydrous Na₂SO₄), filtered, evaporated to dryness and dried in vacuo. The crude product was chromatographed on a silica gel column (Merck, 70 g.), eluting the column with EtOAc:Hexane mixtures (1:3; 1:1) to give pure title compound (202 mg) and impure product. A second chromatography gave title compound as a syrup (total of 292.1 mg, 59.3%) with consistent ¹H-NMR and ¹³C-NMR spectral data. TLC: $R_f$ 0.32 (Silica gel; EtOAc:Hexane—1:1; UV).

C.

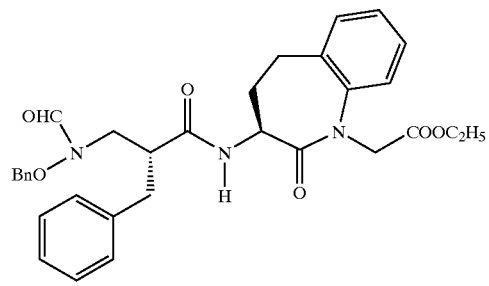

A cooled solution of HCOOH (5.0 ml) was treated with acetic anhydride (Ac2O) (0.5 ml) and stirred at 0° C. for 30 minutes. A solution of Part B compound (288 mg, 0.54 mmole) in dry THF (1.5 ml) was cooled to 0° C. (ice-salt bath), treated with the above Ac₂O/HCOOH mixture (3.4 ml) and stirred at 0° C. for 1.0 hour. The reaction mixture was evaporated to dryness and the residual syrup was dissolved in EtOAc (40 ml), washed with saturated NaHCO₃ (5.0 ml) and brine (5.0 ml), dried (anhydrous Na₂SO₄), filtered, evaporated to dryness, evaporated from toluene and dried in vacuo to give title compound as a syrup (311.3 mg, 100% crude) with consistent ¹H-NMR and ¹³C-NMR spectral data. TLC: $R_f$ 0.18 (Silica gel; EtOAc:Hexane (1:1; UV).

D.

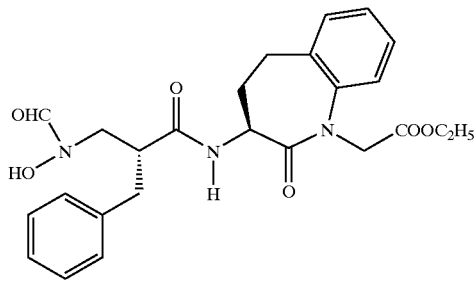

A solution of Part C compound (311 mg) in CH$_3$OH (10 ml) was treated with 10% Pd/C (53 mg) and hydrogenated (balloon) at room temperature for 2.0 hours. The reaction mixture was diluted with CH$_3$OH (10 ml) and filtered through a Celite® pad in a millipore unit, washing the pad well with CH$_3$OH (3×10 ml). The clear filtrate was evaporated to dryness and dried in vacuo to give title compound as a syrup (256.7 mg, 100% crude) with consistent $^1$H-NMR and $^{13}$C-NMR data. TLC: R$_f$ 0.25 (Silica gel; CH$_2$Cl$_2$:MeOH—9:1; UV).

E. [S-(R*,R*)]-3-[[3-(Formylhydroxyamino)-1-oxo-2-(phenylmethyl)propyl]amino]-2,3,4,5-tetrahydro-2-oxo-1H-benzazepine-1-acetic acid A solution of Part D compound (256.7 mg) in CH$_3$OH (3.5 ml) was treated with 1.0 N NaOH (2.17 ml, 4 eq) and stirred at room temperature for 1.0 hour under argon. The reaction mixture was brought to pH 1.0 with 5% KHSO$_4$ (9.45 ml), extracted with EtOAc (40 ml) and the organic extract washed with brine (5.0 ml), dried (anhydrous Na$_2$SO$_4$), filtered, evaporated to dryness and dried in vacuo. The crude product was triturated with CH$_2$Cl$_2$:Hexane (1:4–25 ml) and hexane (20 ml) then dried in vacuo to give title compound as an amorphous off-white solid (215.6 mg, 90.4%) with consistent MS, IR, $^1$H-NMR and analytical data.

TLC: R$_f$ 0.30 (Silica gel; EtOAc:HOAc—95:5; UV).

[α]$_D$=−332.8° (c 0.558, CH$_3$OH).

HPLC: t$_R$=5.21 min (95.8% R isomer); t$_R$=9.58 min (3.59% S isomer); YMC S3 ODS-A 150×6 mm; 220 nm, flow rate=1.5 ml/min; 56% (10% H$_2$O-90% CH$_3$OH-0.2% H$_3$PO$_4$)/44% (90% H$_2$O-10% CH$_3$OH-0.2% H$_3$PO$_4$), isocratic.

Anal. Calc'd for C$_{23}$H$_{25}$N$_3$O$_6$: C, 62.86; H, 5.73; N, 9.56. Found: C, 62.88; H, 5.98; N, 9.20.

EXAMPLE 5

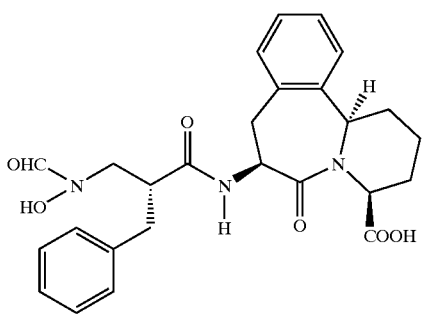

A.

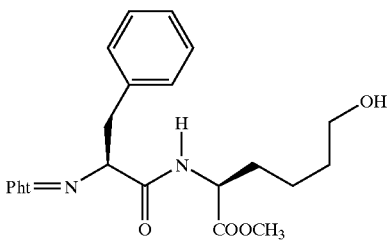

A solution of L-hydroxynorleucine (2.0 g, 13.6 mmoles) in dry methanol (70 ml) was saturated with HCl gas until a clear yellow solution was obtained. The reaction mixture was cooled to room temperature, stirred for 2.0 hours, evaporated to dryness, evaporating the syrup once from toluene (100 ml) then evaporated in vacuo to give the ester as a yellow oil. The crude ester was dissolved in dry CH$_2$Cl$_2$ (50 ml) and dry DMF (15 ml), treated with NMM (2.5 ml, 22.7 mmoles) and cooled to 0° C. (ice-salt bath). The mixture was treated with N-phthaloyl-L-phenyl-alanine (4.0 g, 13.6 mmoles), HOBt.H$_2$O (1.89 g, 13.99 mmoles) and EDAC (2.87 g, 14.98 mmoles), stirred at 0° C. for 25 minutes and at room temperature for 2.0 hours.

The reaction mixture was partitioned between EtOAc (2×200 ml) and H$_2$O (60 ml) and the combined organic extracts were washed sequentially with 0.5 N HCl (60 ml), H$_2$O (60 ml), ½ saturated NaHCO$_3$ (60 ml) and brine (60 ml), dried (anhydrous Na$_2$SO$_4$), filtered, evaporated to dryness and dried in vacuo. The crude product mixture was chromatographed on a silica gel column (Merck, 200 g), eluting the column with EtOAc to give the desired product as a syrup (4.0 g). An additional 321 mg was obtained on re-chromatography of the impure fractions to give title compound (4.32 g, 73%) with consistent $^1$H-NMR and $^{13}$C-NMR spectral data.

TLC: R$_f$ 0.43 (Silica gel; EtOAc; UV).

B.

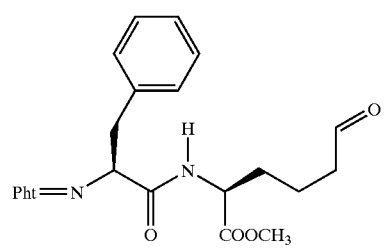

A solution of oxalyl chloride (1.02 ml, 11.7 mmoles) in dry CH$_2$Cl$_2$ (56 ml), was cooled to −78° C. (dry-ice-acetone bath), treated with a solution of dry DMSO (1.67 ml, 21.6 mmoles) in CH$_2$Cl$_2$ (2.0 ml) and stirred at −78° C. for 20 minutes. The mixture was treated with a solution of Part A compound (4.29 g, 9.78 mmoles) in dry CH$_2$Cl$_2$ (22 ml), stirred at −78° C. for another 15 minutes, then treated with triethylamine (8.4 ml). The reaction mixture was stirred at −78° C. for 5.0 minutes, allowed to come to room temperature over a period of 45 minutes, then partitioned between EtOAc (200 ml) and 0.5 N HCl (2×20 ml). The organic phase was washed with brine (40 ml), dried (anhydrous Na$_2$SO$_4$), filtered, evaporated to dryness and dried in vacuo to give title compound as a thick syrup (4.428 g, 100% crude yield), with consistent $^1$H-NMR and $^{13}$C-NMR spectral data.

TLC: R$_f$ 0.73 (Silica gel; EtOAc; UV).

C.

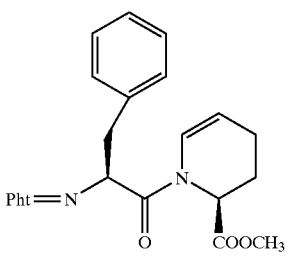

A mixture of Part B compound (4.428 g, 9.78 moles) and TFA (0.20 ml, 2.6 mmoles) in dry $CH_2Cl_2$ (62 ml) was refluxed under argon for 2.0 hours. The reaction mixture was cooled to room temperature, washed with ½ saturated $NaHCO_3$ (20 ml) and brine (20 ml), dried (anhydrous $Na_2SO_4$), filtered, evaporated to dryness and dried in vacuo. The crude product mixture was chromatographed on a silica gel column (Merck, 200 g), eluting the column with $CH_2Cl_2$:EtOAc (9:1) to give the desired product as a syrup. The syrup was triturated with $Et_2O$:Hexane (2:1–60 ml) to give title compound as a white precipitate (2.92 g, 72%; m.p. 141–143° C.) with consistent $^1$H-NMR and $^{13}$C-NMR spectral data.

TLC: $R_f$ 0.67 (Silica gel; $CH_2Cl_2$:EtOAc—9:1; UV).

D.

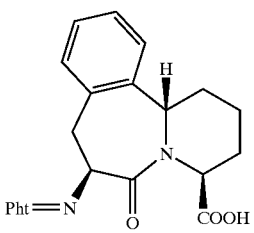

A solution of Part C compound (2.923 g, 6.99 mmoles) in dry $CH_2Cl_2$ (14 ml) was treated with triflic acid (4.15 ml, 6.7 eq) and the resulting yellow solution was stirred at room temperature for 20 hours. The reaction mixture was then poured into ice-water (100 ml), extracted with EtOAc (3×100 ml) and the combined organic extracts washed with $H_2O$ (2×25 ml) and brine (25 ml), dried (anhydrous $Na_2SO_4$), filtered, evaporated to dryness and dried in vacuo. The crude product mixture was chromatographed on a silica gel column (Merck), eluting the column with EtOAc:Hexane mixtures (1:1; 2:1) and EtOAc:HOAc (100:1). The desired fractions were combined, evaporated to dryness and dried in vacuo to give impure title compound as a solid foam (1.238 g, 42%) with consistent $^1$H-NMR and $^{13}$C-NMR spectral data.

TLC: $R_f$ 0.73 (Silica gel; EtOAc:HOAc—95:5; UV).

E.

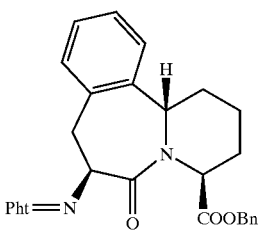

A solution of Part D compound (1.238 g, 3.06 mmoles) in dry DMF (3.5 ml) was treated sequentially with benzyl bromide (0.35 ml, 2.94 mmoles) and $Cs_2CO_3$ (450 mg, 1.38 moles) then stirred at room temperature for 3.0 hours. The mixture was diluted with EtOAc (50 ml), washed with $H_2O$ (5.0 ml), 0.5 N HCl (5.0 ml) and brine (5.0 ml), dried (anhydrous $Na_2SO_4$), filtered, evaporated to dryness and dried in vacuo. The crude product (1.63 g) was chromatographed on a silica gel column (Merck), eluting the column with EtOAc:Hexane (1:3) to give title compound as a syrup (586.4 mg, 39%) with consistent $^1$H-NMR and $^{13}$C-NMR spectral data.

TLC: $R_f$ 0.45 (Silica gel; EtOAc:Hexane—1:1; UV).

F.

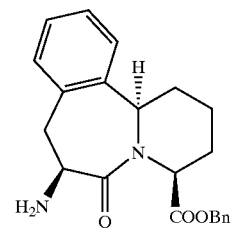

A solution of Part E compound (586 mg, 1.18 mmoles) in dry methanol (15 ml) was treated with $NH_2NH_2.H_2O$ (66 µl, 1.2 eq) and stirred at room temperature for 48 hours. The reaction mixture was diluted with $Et_2O$ (50 ml) and filtered through a millipore unit, washing the solids well with $Et_2O$ (40 ml). The clear solution was evaporated to dryness and the solids obtained were suspended in $CH_2Cl_2$ (90 ml) and the solution filtered through a millipore unit, washing the solids well with $CH_2Cl_2$ (40 ml). The combined organic extracts were washed with brine (15 ml), dried (anhydrous $Na_2SO_4$), filtered, evaporated to dryness and dried in vacuo to give title compound as a thick syrup (351 mg, 82%) with a consistent $^1$H-NMR spectrum.

TLC: $R_f$ 0.42 ($CH_2Cl_2$:MeOH—9:1; UV, Ninhydrin).

G.

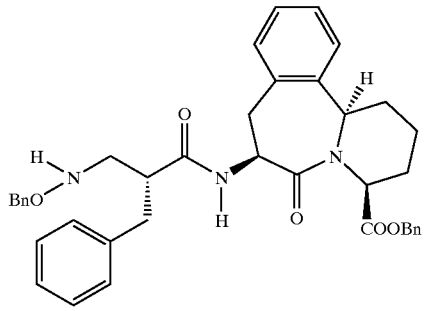

Example 3 Part A ephedrine salt (538 mg, 1.2 mmoles), was partitioned between 5% $KH_2PO_4$ (adjusted to pH 2.5; 5.4 ml) and EtOAc (2×22 ml) and the combined organic extracts were washed with brine (5.4 ml), dried (anhydrous $Na_2SO_4$), filtered, evaporated to dryness and dried in vacuo to give the free acid of the ephedrine salt as a clear syrup (323 mg, 100% crude yield).

A solution of the free acid in dry $CH_2Cl_2$ (8.0 ml) was cooled to 0° C. (ice-salt bath) and treated sequentially with a solution of Part F compound (351 mg, 0.96 mmole) in dry $CH_2Cl_2$ (2.0 ml), $HOBT.H_2O$ (163 mg, 1.2 mmoles) and EDAC (240 mg, 1.25 mmoles). The reaction mixture was stirred at 0° C. for 1.0 hour, at room temperature for 1.5 hours, then partitioned between EtOAc (40 ml) and $H_2O$ (5.0 ml). The organic extracts were washed with 5% $KH_2PO_4$ (adjusted to pH 2.5; 5.0 ml), $H_2O$ (5.0 ml), saturated $NaHCO_3$ (5.0 ml) and brine (5.0 ml), dried (anhydrous $Na_2SO_4$), filtered, evaporated to dryness and dried in vacuo. The crude product (810 mg) was chromatographed on a silica gel column (Merck), eluting the column with EtOAc:Hexane (1:3) to give pure title compound (494 mg, 65%) as a solid foam with consistent ¹H-NMR and ¹³C-NMR spectral data.

TLC: $R_f$ 0.45 (Silica gel; EtOAc:Hexane—1:1; UV).

H.

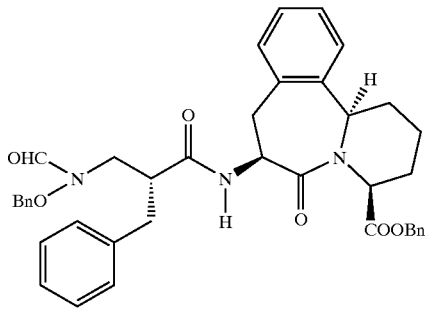

A cooled solution (0° C., ice-salt bath) of HCOOH (5.0 ml) was treated with Ac₂O (0.5 ml) and stirred at 0° C. for 30 minutes. A solution of Part G compound (493 mg, 0.78 mmole) in dry THF (2.2 ml) was cooled to 0° C. (ice-salt bath), treated with the above Ac₂O/HCOOH mixture (4.9 ml) and stirred at 0° C. for 1.5 hours. The reaction mixture was evaporated to dryness, evaporated from Et₂O (50 ml) and the residual syrup was dissolved in EtOAc (60 ml), washed with saturated NaHCO₃ (7.0 ml) and brine (7.0 ml), dried (anhydrous Na₂SO₄), filtered, evaporated to dryness, evaporated from toluene and dried in vacuo to give title compound as a syrup (558.3 mg, 100% crude) with consistent ¹H-NMR and ¹³C-NMR spectral data.

TLC: $R_f$ 0.2 (Silica gel; EtOAc:Hexane—1:1; UV).

I.

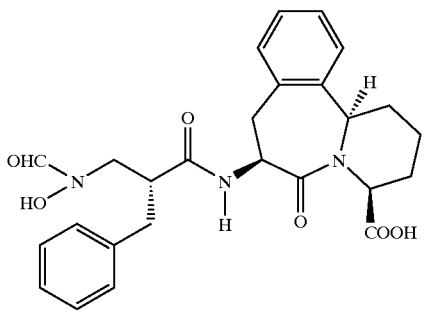

A solution of Part H compound (535 mg, 0.78 mmole) in CH₃OH (15 ml) was treated with 10% Pd/C (83 mg) and hydrogenated (balloon) at room temperature for 4.0 hours. The reaction mixture was diluted with CH₃OH (15 ml) and filtered through a celite pad in a millipore unit, washing the pad well with CH₃OH (3×15 ml). The clear filtrate was evaporated to dryness and dried in vacuo to give a syrup (354.8 mg) which was triturated with CH₂Cl₂:Hexane (1:5–30 ml) and hexane (25 ml) then dried in vacuo. Title compound was obtained as an off-white solid foam (348.5 mg, 90%).

TLC: $R_f$ 0.38 (Silica gel; CH₂Cl₂:MeOH—9:1; UV).
MS (M+H)⁺=480.
$[\alpha]_D$=+44.6° (c 0.52, CH₃OH).
HPLC: $t_R$=11.72 min (95.9%); YMC S3 ODS-A 150×6 mm; 220 nm, flow rate=1.5 ml/min; 55% (10% H₂O-90% CH₃OH-0.2% H₃PO₄)/45% (90% H₂O-10% CH₃OH-0.2% H₃PO₄), isocratic.
Anal. Calc'd for C₂₆H₂₉N₃O₆·0.4H₂O·0.14 Hexane (Eff. Mol. Wt.=497.08): C, 64.63; H, 6.83; N, 8.46. Found: C, 64.24; H, 6.43; N, 8.12.

The following are examples of additional compounds of the invention which may be prepared employing procedures set out hereinbefore and in the working Examples.

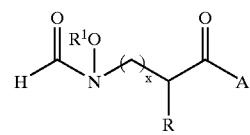

| Example No. | R¹ | x | R | A |
|---|---|---|---|---|
| 6 | H | 1 | CH₂Ph | 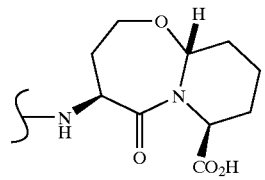 |
| 7 | H | 1 | CH₂Ph | 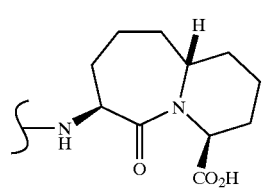 |

-continued
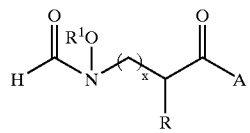
| Example No. | R¹ | x | R | A |
|---|---|---|---|---|
| 8 | H | 1 | CH$_2$CH(CH$_3$)$_2$ | 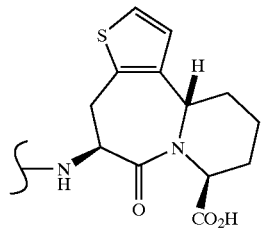 |
| 9 | H | 1 | CH$_2$Ph | 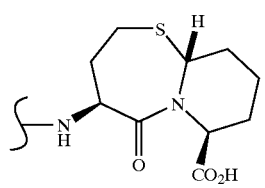 |
| 10 | H | 1 | CH$_2$CH(CH$_3$)$_2$ | 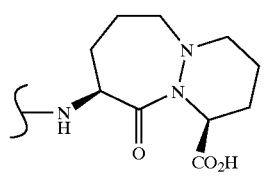 |
| 11 | H | 1 | CH$_2$Ph | 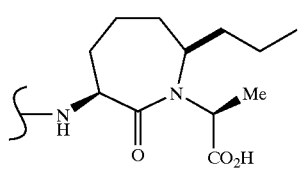 |
| 12 | H | 1 | CH$_2$Ph | 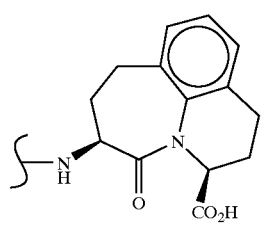 |
| 13 | H | 1 | (CH$_2$)$_3$-C$_6$H$_4$-OMe | 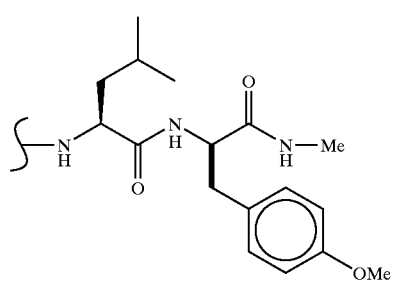 |

-continued
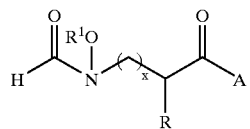
| Example No. | $R^1$ | x | R | A |
|---|---|---|---|---|
| 14 | H | 1 | $CH(CH_3)_2$ | 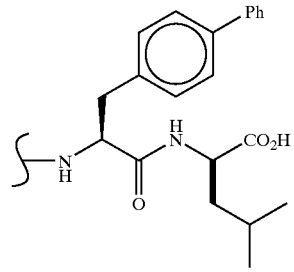 |
| 15 | H | 1 | $CH(CH_3)_2$ | 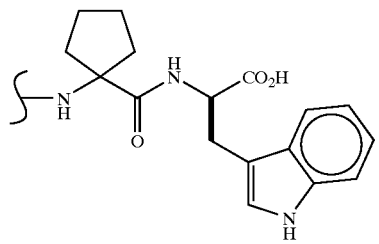 |
| 16 | H | 1 | $CH(CH_3)_2$ | 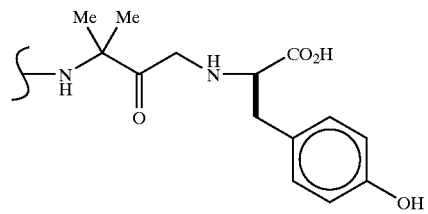 |
| 17 | H | 1 | $CH_2Ph$ | 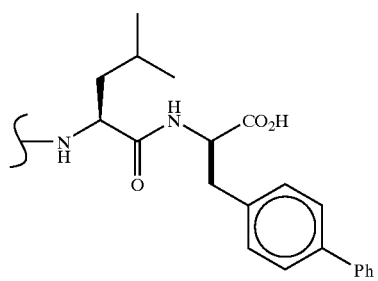 |
What is claimed is:
1. A compound of the formula
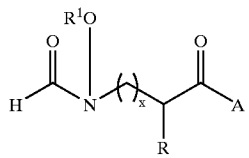
or a pharmaceutically acceptable salt thereof wherein
x is 0 or 1, $R^1$ is H,
R is alkyl or arylalkyl,
p is 0 or an integer from 1 to 8; and
A is a conformationally restricted dipeptide mimic which has the structure
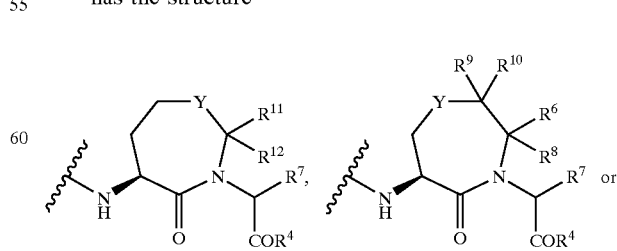

-continued

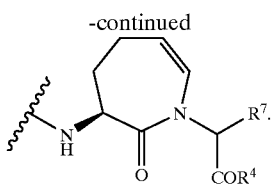

where Y is $CH_2$,
$R^7$, $R^8$ and $R^9$ are independently selected from hydrogen, alkyl, alkenyl, cycloalkyl-$(CH_2)_m$—, aryl-$(CH_2)_m$— and heteroaryl-$(CH_2)_m$—,
where m is 0 or an integer from 1 to 6;
$R^6$, $R^{10}$, $R^{11}$, and $R^{12}$ are independently selected from hydrogen, alkyl, alkenyl, cycloalkyl-$(CH_2)_p$—, aryl-$(CH_2)_p$— and heteroaryl-$(CH_2)_p$—; and
$R^4$ is OH
wherein the term heteroaryl alone or as part of another group refers to an aromatic ring which may optionally contain at most one sulfur atom or at most one oxygen atom and/or one to four nitrogen atoms, provided that the total number of heteroatoms in the ring is 4 or less, which aromatic ring may be optionally substituted with one, two or three substituents, and which aromatic ring may be fused to a benzene ring or a pyridyl ring to form a bicyclic ring which may be optionally substituted.

2. The compound which is

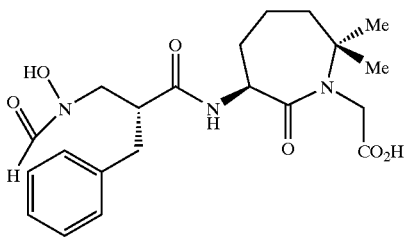

or a pharmaceutically acceptable salt thereof.

* * * * *